(12) United States Patent
Kura et al.

(10) Patent No.: US 8,916,621 B2
(45) Date of Patent: Dec. 23, 2014

(54) PHOTORESIST COMPOSITIONS

(71) Applicant: BASF SE, Ludwigshafen (DE)

(72) Inventors: Hisatoshi Kura, Hyogo (JP); Kaori Sameshima, Osaka (JP); Kazuhiko Kunimoto, Hyogo (JP); Peter Nesvadba, Marly (CH); Masaki Ohwa, Hyogo (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/939,387

(22) Filed: Jul. 11, 2013

(65) Prior Publication Data

US 2013/0302728 A1    Nov. 14, 2013

Related U.S. Application Data

(62) Division of application No. 13/255,543, filed as application No. PCT/EP2010/053468 on Mar. 17, 2010, now Pat. No. 8,507,569.

(30) Foreign Application Priority Data

Mar. 23, 2009 (EP) .................................. 09155860

(51) Int. Cl.
| | | |
|---|---|---|
| C08F 2/46 | (2006.01) | |
| C08G 61/04 | (2006.01) | |
| G03F 7/00 | (2006.01) | |
| C08F 110/06 | (2006.01) | |
| C08F 265/02 | (2006.01) | |
| C08F 110/02 | (2006.01) | |
| G03F 7/031 | (2006.01) | |
| G03F 7/40 | (2006.01) | |
| C07D 491/113 | (2006.01) | |
| C08K 5/3435 | (2006.01) | |
| G03F 7/028 | (2006.01) | |
| C07D 211/94 | (2006.01) | |

(52) U.S. Cl.
CPC .............. *G03F 7/028* (2013.01); *G03F 7/0007* (2013.01); *C08F 110/06* (2013.01); *C08F 265/02* (2013.01); *C08F 110/02* (2013.01); *G03F 7/031* (2013.01); *G03F 7/40* (2013.01); *C07D 491/113* (2013.01); *C08K 5/3435* (2013.01); *C07D 211/94* (2013.01)
USPC .................................................. 522/1; 520/1

(58) Field of Classification Search
CPC .......... B29C 59/16; G03G 5/062; C08F 2/50; C08F 2/46
USPC .................................................. 522/1; 520/1
See application file for complete search history.

(56) References Cited

U.S. PATENT DOCUMENTS

| | | | |
|---|---|---|---|
| 4,105,626 A | | 8/1978 | Brunetti et al. |
| 4,212,974 A | | 7/1980 | Higashida et al. |
| 5,124,378 A | * | 6/1992 | Behrens et al. ................. 524/95 |
| 5,300,647 A | * | 4/1994 | Malherbe et al. ............. 546/188 |
| 5,398,976 A | | 3/1995 | Webb |
| 5,719,008 A | * | 2/1998 | Hozumi et al. ............ 430/287.1 |
| 5,800,952 A | * | 9/1998 | Urano et al. ...................... 430/7 |
| 5,821,016 A | | 10/1998 | Satoh et al. |
| 5,847,015 A | * | 12/1998 | Tajima et al. ................... 522/75 |
| 5,863,678 A | | 1/1999 | Urano et al. |
| 5,866,298 A | | 2/1999 | Iwamoto et al. |
| 5,879,855 A | | 3/1999 | Schadeli et al. |
| 5,882,843 A | | 3/1999 | Kudo et al. |
| 6,900,268 B2 | | 5/2005 | Fink et al. |
| 7,230,042 B2 | | 6/2007 | Roth et al. |
| 7,358,311 B2 | | 4/2008 | Roth et al. |
| 2004/0265509 A1 | * | 12/2004 | Roth et al. ..................... 428/1.1 |
| 2006/0128903 A1 | | 6/2006 | Roth et al. |
| 2006/0172080 A1 | | 8/2006 | Wolf et al. |
| 2008/0234453 A1 | | 9/2008 | Roth et al. |

(Continued)

FOREIGN PATENT DOCUMENTS

| | | |
|---|---|---|
| EP | 0126541 | 11/1984 |
| EP | 0309400 | 3/1989 |

(Continued)

OTHER PUBLICATIONS

Kudo, Takanori et al, Pigmented Photoresists for Color Filters, 1996, Journal of Photopolymer Science and Technology, vol. 9, No. 1, 109-120.*
Kudo, T. et al.,"Fabrication Process of Color Filters Using Pigmented Photoresists", Jpn. J. Appl. Phys., 1998, vol. 37, p. 3594.
Kudo T. et al., "Pigment Photoresists for Color Filters", J. Photopolym. Sci. Technol., 1996, vol. 9, p. 109.

(Continued)

*Primary Examiner* — Ling Choi
*Assistant Examiner* — Jessica E Whiteley
(74) *Attorney, Agent, or Firm* — Shruti Costales

(57) ABSTRACT

The present invention relates to a radically polymerizable composition comprising a hydroxylamine ester used to manufacture color filters. The invention further relates to novel hydroxylamine esters. The invention further relates to the use of hydroxylamine esters in all liquid crystal display components requiring post-baking.
The present invention relates to a radically polymerizable composition comprising:
(a) at least one alkaline developable resin;
(b) at least one acrylate monomer;
(c) at least a photoinitiator;
(d) at least one hydroxylamine ester compound of formula I

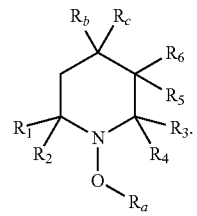

2 Claims, No Drawings

(56) References Cited

U.S. PATENT DOCUMENTS

| | | |
|---|---|---|
| 2010/0086881 A1 | 4/2010 | Matsumoto et al. |
| 2010/0136467 A1 | 6/2010 | Matsumoto et al. |
| 2010/0136491 A1 | 6/2010 | Matsumoto et al. |

FOREIGN PATENT DOCUMENTS

| | | |
|---|---|---|
| EP | 0320264 | 6/1989 |
| EP | 0339841 | 11/1989 |
| EP | 0438123 | 7/1991 |
| EP | 0441232 | 8/1991 |
| EP | 0497531 | 8/1992 |
| EP | 0 309 400 * | 2/1994 |
| EP | 0780729 | 6/1997 |
| EP | 0881541 | 12/1998 |
| EP | 0902327 | 3/1999 |
| EP | 1601719 | 12/2005 |
| EP | 1655303 | 5/2006 |
| GB | 2180358 | 3/1987 |
| JP | 4964635 | 6/1974 |
| JP | 5742009 | 3/1982 |
| JP | 01130103 | 5/1989 |
| JP | 01134306 | 5/1989 |
| JP | 05173320 | 7/1993 |
| JP | 06230212 | 8/1994 |
| JP | 08305019 | 11/1996 |
| JP | 09179299 | 7/1997 |
| JP | 09269410 | 10/1997 |
| JP | 09325209 | 12/1997 |
| JP | 10010718 | 1/1998 |
| JP | 10090516 | 4/1998 |
| JP | 10171119 | 6/1998 |
| JP | 10221843 | 8/1998 |
| JP | 11174459 | 7/1999 |
| JP | 11174464 | 7/1999 |
| JP | 2000081701 | 3/2000 |
| JP | 2002206014 | 7/2002 |
| JP | 2003015288 | 1/2003 |
| JP | 2003128957 | 5/2003 |
| JP | 2003215790 | 7/2003 |
| JP | 2003233176 | 8/2003 |
| JP | 2003330184 | 11/2003 |
| JP | 2004069754 | 3/2004 |
| JP | 2004527627 | 9/2004 |
| JP | 2004302245 | 10/2004 |
| JP | 2005504158 | 2/2005 |
| JP | 2005077451 | 3/2005 |
| JP | 2005527669 | 9/2005 |
| JP | 2005316449 | 11/2005 |
| JP | 2005338328 | 12/2005 |
| JP | 2006036750 | 2/2006 |
| JP | 3754065 | 3/2006 |
| JP | 2007530723 | 11/2007 |
| WO | 0190113 | 11/2001 |
| WO | 03029332 | 4/2003 |
| WO | 2004081100 | 9/2004 |
| WO | 2005080337 | 9/2005 |
| WO | 2006027327 | 3/2006 |
| WO | 2007062963 | 6/2007 |
| WO | 2007071497 | 6/2007 |
| WO | 2008155247 | 12/2008 |

OTHER PUBLICATIONS

English language machine-generated translation of JP2003015288 (14 Pages); 2003.
English language machine-generated translation of JP2002206014 (22 Pages); 2002.
English language machine-generated translation of JP2004069754 (18 Pages); 2004.
English language machine-generated translation of JP2004302245 (13 Pages); 2004.
English language machine-generated translation of JP2005077451 (20 Pages); 2005.
English language machine-generated translation of JP2005316449 (25 Pages); 2005.
English language machine-generated translation of JP2005338328 (24 Pages); 2005.
English language machine-generated translation of JP3754065 (23 Pages); 2006.
English language machine-generated translation of JP10221843 (16 Pages); 1998.
English language machine-generated translation of JP05173320 (15 Pages); 1993.
English language machine-generated translation of JP06230212 (10 Pages); 1994.
English language machine-generated translation of JP09269410 (20 Pages); 1997.
English language machine-generated translation of JP10090516 (14 Pages); 1998.
English language machine-generated translation of JP10171119 (13 Pages); 1998.
English language machine-generated translation of JP09179299 (50 Pages); 1997.
English language machine-generated translation of JP09325209 (8 Pages); 1997.
English language machine-generated translation of JP08305019 (49 Pages); 1996.
English language machine-generated translation of JP2000081701 (12 Pages); 2000.
English language machine-generated translation of JP11174459 (7 Pages); 1999.
English language machine-generated translation of JP11174464 (8 Pages); 1999.
English language machine-generated translation of JP2006036750 (34 Pages); 2006.
English language machine-generated translation of EP0441232 (10 Pages); 1991.
English language abstract of JP5742009 (2 Pages); 1982.
English language abstract of JP01130103 (2 Pages); 1989.
English language abstract of JP01134306 (2 Pages); 1989.
English language abstract of JP10010718; 1998.
English language abstract of JP2003128957; 2003.
English language abstract of JP200330184; 2003.
English language machine-generated translation of JP2003-215790 (18 Pages); 2003.
English language machine-generated translation of JP2003-233176 (20 Pages); 2003.

* cited by examiner

PHOTORESIST COMPOSITIONS

CROSS-REFERENCE TO RELATED APPLICATIONS

This application is a divisional of U.S. patent application Ser. No. 13/255,543 filed on Sep. 30, 2011, which is the National Stage of International Application PCT/EP2010/053468 filed Mar. 17, 2010, which claims priority to EP 09155860.1 filed Mar. 23, 2009, wherein the contents of all applications are herein incorporated by reference.

FIELD OF THE INVENTION

The present invention relates to a radically polymerizable composition comprising a hydroxylamine ester used to manufacture color filters. The invention further relates to novel hydroxylamine esters. The invention further relates to the use of hydroxylamine esters in all liquid crystal display components requiring post-baking.

BACKGROUND OF THE INVENTION

Color filter (CF) for liquid crystal display (LCD), which comprises black matrix and red, green and blue color pixels on a glass substrate, is manufactured by photolithography using radically photopolymerizable resists. After the photolithographic process, post-baking by heating for example at 230° C. for 30 min is normally performed to polymerize remaining acrylic double bonds to attain required durability in the production process of CF/LCD and for long-term survival in LCD as permanent coat. In the market there is a strong demand for lower temperature and/or shorter time in the post-baking process for following reasons:
1) use of thermally less stable but inexpensive soda-lime glass as substrate for cost reduction,
2) reduction of energy consumption,
3) shorter tact time for higher productivity and/or
4) more freedom in choice of materials for CF.

Low temperature curing might be required for other resists and curing compositions used for manufacturing of Displays besides color filter resists.

Resist makers have attempted to attain low temperature curing CF resist by use of existing thermal radical initiators like peroxides.

JP10010718 discloses a color former, which includes organic peroxides as thermal polymerization initiators and production of a color filter having good solvent resistance by applying post-baking process, preferably at 100-180° C., after photolithography process.

JP2003330184 discloses a colored photosensitive resin composition capable of forming a color filter having high heat resistance, high hardness and high solvent resistance even after the resin composition is subjected to heat treatment of comparatively low temperature. The resin is composed of a polymerization initiator having an oxadiazole structure or a triazine structure containing a trihalomethyl group.

JP2003128957 provides a curable composition for forming a protective film capable of providing the protective film having various excellent physical properties even when the protective film is formed at a temperature not higher than the deformation temperature or discoloration temperature of a resin substrate. This curable composition comprises (A) a copolymer of (a1) an unsaturated carboxylic acid and/or an unsaturated carboxylic acid anhydride, (a2) an epoxy group-containing unsaturated compound and (a3) an olefinically unsaturated compound other than the monomers (a1) and (a2), (B) an epoxy resin other than the component (A) and (C) a compound capable of producing an acid with heat or radiations. The protective film is formed from the curable composition; The method for forming the protective film comprises coating the top surface of the resin substrate with the curable composition and then carrying out heat and/or light treatment. The treatment is carried out at a temperature without exceeding 180° C.

JPA2003015288 discloses a radiation sensitive composition, including thermal polymerization initiators like organic peroxides, hydroperoxide and azo compounds, capable of forming a color filter having satisfactory adhesion to a plastics substrate even if such low temperature treatment as not to cause deformation or yellowing to the plastics substrate is adopted when the color filter is formed on the plastics substrate and to provide a color filter formed form the composition. The radiation sensitive composition contains (A) a colorant, (B) an alkali-soluble resin, (C) a polyfunctional monomer, (D) a photopolymerization initiator and (E) a thermal polymerization initiator.

The European patent EP309400 (Ciba) describes N-acyloxy hindered amine stabilizers to stabilize an ambient curable or acid catalyzed thermosetting coating composition.

Hydroxylamine esters are known as thermal initiators to polymerize ethylenically unsaturated monomers.

The International Publication WO2001090113 (Ciba) describes polymerizable compositions comprising hydroxylamine esters and an ethylenically unsaturated monomer or oligomer.

The International Publication WO03029332 (Ciba) relates to a process for crosslinking unsaturated polymer resins as e.g. unsaturated polyesters using hydroxylamine esters as radical source.

The International Publication WO04081100 (Ciba) relates to a dual thermal and ultraviolet radiation curable coating composition, comprising at least an ethylenically unsaturated compound and a hydroxylamine ester as thermal initiator.

The international Publication WO2006027327 (Ciba) relates to the degradation of polypropylene with hydroxylamine ester compositions.

It has been found that the use of hydroxylamine esters as disclosed in WO2006027327 as thermal radical initiators for radically polymerizable compositions used to manufacture color filters results in a sufficiently high C═C conversion surprisingly at lower temperature and/or in shorter time in the thermal curing (post baking) process which takes place after the photo curing process both in comparison to corresponding compositions lacking these hydroxylamine esters and in comparison to corresponding compositions comprising other thermal radical initiators (TRIs), e.g. peroxides, than these hydroxylamine esters.

SUMMARY OF THE INVENTION

Thus, the invention relates to a radically polymerizable composition comprising:
(a) at least one alkaline developable resin;
(b) at least one acrylate monomer;

(c) at least one photoinitiator; and
(d) at least one hydroxylamine ester compound of formula I

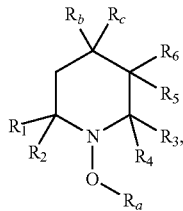
(I)

wherein
$R_a$ represents an acyl radical;
one of $R_b$ and $R_c$ represents hydrogen and the other one represents a substituent; or
$R_b$ and $R_c$ both represent hydrogen or identical or different substituents; or
$R_b$ and $R_c$ together represent oxygen; or
$R_b$ and $R_c$ together form a ring;
$R_1$-$R_4$ each represent $C_1$-$C_6$alkyl; and
$R_5$ and $R_6$ each represent independently of one another hydrogen, $C_1$-$C_6$alkyl or $C_6$-$C_{10}$aryl; or $R_5$ and $R_6$ together represent oxygen.

DETAILED DESCRIPTION OF THE INVENTION

Definitions:

The alkaline developable resin has free carboxylic groups, acid value from 10 to 600 mg KOH (potassium hydroxide)/g, preferably 20 to 300 mg KOH/g and a molecular weight of about 1'000 to 1'000'000, preferably 2'000 to 200'000.

Examples of alkali developable resins are acrylic polymers having carboxylic acid function as a pendant group, such as copolymers obtained by copolymerizing an ethylenic unsaturated carboxylic acid such as (meth)acrylic acid, 2-carboxyethyl (meth)acrylic acid, 2-carboxypropyl (meth)acrylic acid, itaconic acid, crotonic acid, maleic acid, maleic anhydride, half-ester of maleic acid, fumaric acid, cinnamic acid, mono[2-(meth)acryloyloxyethyl]succinate, mono[2-(meth)acryloyloxyethyl]adipate, mono[2-(meth)acryloyloxyethyl]phthalate, mono[2-(meth)acryloyloxyethyl]hexahydrophthalate, mono[2-(meth)acryloyloxyethyl]maleate, mono[2-(meth)acryloyloxypropyl]succinate, mono[2-(meth)acryloyloxypropyl]adipate, mono[2-(meth)acryloyloxypropyl]phthalate, mono[2-(meth)acryloyloxypropyl]hexahydrophthalate, mono[2-(meth)acryloyloxypropyl]maleate, mono[2-(meth)acryloyloxybutyl]succinate, mono[2-(meth)acryloyloxybutyl]adipate, mono[2-(meth)acryloyloxybutyl]phthalate, mono[2-(meth)acryloyloxybutyl]hexahydrophthalate, mono[2-(meth)acryloyloxybutyl]maleate, 3-(alkylcarbamoyl)acrylic acid, α-chloro-acrylic acid, maleic acid, monoesterified maleic acid, citraconic acid and ω-carboxypolycaprolactone mono(meth)acrylate, with one or more monomers selected from esters of (meth)acrylic acid, such as methyl (meth)acrylate, ethyl (meth)acrylate, propyl (meth)acrylate, butyl (meth)acrylate, benzyl (meth)acrylate, 2-ethylhexyl (meth)acrylate, hydroxyethyl (meth)acrylate, hydroxypropyl (meth)acrylate, tetrahydrofurfuryl (meth)acrylate, hydroxybutyl (meth)acrylate, glycerol mono (meth)acrylate, dihydroxypropyl (meth)acrylate, allyl (meth)acrylate, cyclohexyl (meth)acrylate, phenyl (meth)acrylate, methoxyphenyl (meth)acrylate, methoxyethyl (meth)acrylate, phenoxyethyl (meth)acrylate, methoxydiethyleneglycol (meth)acrylate, methoxytriethyleneglycol (meth)acrylate, methoxypropyl (meth)acrylate, methoxydipropyleneglycol (meth)acrylate, isobornyl meth(acrylate), dicyclopentadienyl (meth)acrylate, 2-hydroxy-3-phenoxypropyl (meth)acrylate, tricyclo[5.2.1.0$^{2,6}$]decan-8-yl (meth)acrylate, aminoethyl (meth)acrylate, N,N-dimethylaminoethyl (meth)acrylate, aminopropyl (meth)acrylate, N,N-dimethylaminopropyl (meth)acrylate, glycidyl (meth)acrylate, 2-methylglycidyl (meth)acrylate, 3,4-epoxybutyl (meth)acrylate, 6,7-epoxyheptyl (meth)acrylate; vinyl aromatic compounds, such as styrene, α-methylstyrene, vinyltoluene, p-chlorostyrene, polychlorostyrene, fluorostyrene, bromostyrene, ethoxymethyl styrene, methoxystyrene, 4-methoxy-3-methystyrene, dimethoxystyrene, vinylbenzyl methyl ether, vinylbenzyl glycidyl ether, indene, 1-methylindene; amide type unsaturated compounds, such as (meth)acrylamide, diacetone acrylamide, N-methylolacrylamide, N-butoxymethacrylamide, N,N-dimethyl (meth)acrylamide, N,N-diethyl (meth)acrylamide, N,N-dibutyl (meth)acrylamide, N,N-diethylhexyl (meth)acrylamide, N,N-dicyclohexyl (meth)acrylamide, N,N-diphenyl (meth)acrylamide, N-methyl-N-phenyl (meth)acrylamide, N-hydroxyethyl-N-methyl (meth)acrylamide, N-methyl (meth)acrylamide, N-ethyl (meth)acrylamide, N-propyl (meth)acrylamide, N-butyl (meth)acrylamide, N-hydroxyethyl (meth)acrylamide, N-heptyl (meth)acrylamide, N-octyl (meth)acrylamide, N-ethyhexyl (meth)acrylamide, N-hydroxyethyl (meth)acrylamidecyclohexyl, N-benzyl (meth)acrylamide, N-phenyl (meth)acrylamide, N-tolyl (meth)acrylamide, N-hydroxyphenyl (meth)acrylamide, N-naphthyl (meth)acrylamide, N-phenylsulfonyl (meth)acrylamide, N-methylphenylsulfonyl (meth)acrylamide and N-(meth)acryloylmorpholine; vinyl or allyl esters, such as vinyl acetate, vinyl propionate, vinyl butylate, vinyl pivalate, vinyl benzoate, vinyl trimethylacetate, vinyl diethylacetate, vinyl barate, vinyl caproate, vinyl chloroacetate, vinyl dichloroacetate, vinyl methoxyacetate, vinyl butoxyacetate, vinyl phenylacetate, vinyl acetate, vinyl acetoacetate, vinyl lactate, vinyl phenylbutylate, vinyl cyclohexylcarboxylate, vinyl salicylate, vinyl chlorobenzoate, vinyl tetrachlorobenzoate, vinyl naphthoate, allyl acetate, allyl propionate, allyl butylate, allyl pivalate, allyl benzoate, allyl caproate, allyl stearate, allyl acetoacetate, allyl lactate; vinyl or allyl ethers, such as vinyl methyl ether, vinyl ethyl ether, vinyl hexyl ether, vinyl octyl ether, vinyl ethylhexyl ether, vinyl methoxyethyl ether, vinyl ethoxyethyl ether, vinyl chloroethyl ether, vinyl hydroxyethyl ether, vinyl ethylbutyl ether, vinyl hydroxyethoxyethyl ether, vinyl dimethylaminoethyl ether, vinyl diethylaminoethyl ether, vinyl butylaminoethyl ether, vinyl benzyl ether, vinyl tetrahydrofurfuryl ether, vinyl phenyl ether, vinyl tolyl ether, vinyl chlorophenyl ether, vinyl chloroethyl ether, vinyl dichlorophenyl ether, vinyl naphthyl ether, vinyl anthryl ether, allyl glycidyl ether; crotonates, such as butyl crotonate, hexyl crotonate, glycerine monocrotonate; itaconates, such as dimethyl itaconate, diethyl itaconate, dibutyl itaconate; and maleates or fumarates, such as dimethyl mareate, dibutyl fumarate; polyolefin type compounds, such as butadiene, isoprene, chloroprene and the like; methacrylonitrile, methyl isopropenyl ketone, vinyl acetate, vinyl propionate, vinyl pivalate, maleimide, N-phenylmaleimide, N-methylphenylmaleimide, N-methoxyphenylmaleimide, N-cyclohexylmaleimide, N-alkylmaleimide, maleic anhydride, polystyrene macromonomer, polymethyl (meth)acrylate macromonomer, polybutyl (meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferable examples of copolymers are copolymers of methyl (meth)acrylate/(meth)acrylic acid, copolymers of benzyl (meth)acrylate/(meth)acrylic acid, copolymers of methyl (meth)acrylate/ethyl (meth)acrylate/ (meth)acrylic acid, copolymers of benzyl (meth)acrylate/ (meth)acrylic acid/styrene, copolymers of benzyl (meth) acrylate/(meth)acrylic acid/hydroxyethyl (meth)acrylate, copolymers of methyl (meth)acrylate/butyl (meth)acrylate/ (meth)acrylic acid/styrene, copolymers of methyl (meth) acrylate/benzyl (meth)acrylate/(meth)acrylic acid/hydroxyphenyl (meth)acrylate, copolymers of methyl (meth) acrylate/(meth)acrylic acid/polymethyl (meth)acrylate macromonomer, copolymers of benzyl (meth)acrylate/ (meth)acrylic acid/polymethyl (meth)acrylate macromonomer, copolymers of tetrahydrofurfuryl (meth)acrylate/styrene/(meth)acrylic acid, copolymers of methyl (meth) acrylate/(meth)acrylic acid/polystyrene macromonomer, copolymers of benzyl (meth)acrylate/(meth)acrylic acid/ polystyrene macromonomer, copolymers of benzyl (meth) acrylate/(meth)acrylic acid/2-hydroxyethyl (meth)acrylate/ polystyrene macromonomer, copolymers of benzyl (meth) acrylate/(meth)acrylic acid/2-hydroxypropyl (meth)acrylate/ polystyrene macromonomer, copolymers of benzyl (meth) acrylate/(meth)acrylic acid/2-hydroxy-3-phenoxypropyl (meth)acrylate/polymethyl (meth)acrylate macromonomer, copolymers of methyl (meth)acrylate/(meth)acrylic acid/2-hydroxyethyl (meth)acrylate/polystyrene macromonomer, copolymers of benzyl (metha)crylate/(meth)acrylic acid/2-hydroxyethyl (meth)acrylate/polymethyl (meth)acrylate macromonomer, copolymers of N-phenylmaleimide/benzyl (meth)acrylate/(meth)acrylic acid and styrene, copolymers of benzyl (meth)acrylate/(meth)acrylic acid/N-phenylmaleimide/mono-[2-(meth)acryloyloxyethyl]succinate/styrene, copolymers of allyl (meth)acrylate/(meth)acrylic acid/N-phenylmaleimide/mono-[2-(meth)acryloyloxyethyl]succinate/styrene, copolymers of benzyl (meth)acrylate/(meth) acrylic acid/N-phenylmaleimide/glycerol mono(meth) acrylate/styrene, copolymers of benzyl (meth)acrylate/ω-carboxypolycaprolactone mono(meth)acrylate/(meth) acrylic acid/N-phenylmaleimide/glycerol mono(meth) acrylate/styrene, and copolymers of benzyl (meth)acrylate/ (meth)acrylic acid/N-cyclohexylmaleimide/styrene. Example of commercial product is Ripoxy SPC-2000 provided by Showa Highpolymer.

The term "(meth)acrylate" in the context of the present application is meant to refer to the acrylate as well as to the corresponding methacrylate.

Other examples of alkaline developable resins are polymers or oligomers having at least two ethylenically unsaturated groups and at least one carboxyl function within the molecule structure, such as a resin obtained by the reaction of a saturated or unsaturated polybasic acid anhydride with a product of the reaction of an epoxy compound and an unsaturated monocarboxylic acid (for example, EB9696 from UCB Chemicals; KAYARAD TCR1025 from Nippon Kayaku Co. LTD.; NK OLIGO EA-6340, EA-7440 from Shin-Nakamura Chemical Co., Ltd.). Other examples of such binders are described in JP2002-206014A, JP2004-69754A, JP2004-302245A, JP2005-77451A, JP2005-316449A, JP2005-338328A and JP3754065B2.

Further examples are reaction products obtained by adding an epoxy group containing unsaturated compound to a part of the carboxyl groups of a carboxylic acid group containing polymer (for ex., ACA200, ACA200M, ACA210P, ACA230AA, ACA250, ACA300, ACA320 from Daicel Chemical Industries, Ltd. and Ripoxy SPC-1000 provided by Showa Highpolymer). As the carboxylic acid containing polymer, the abovementioned binder polymers which are resulting from the reaction of an unsaturated carboxylic acid compound with one or more polymerizable compounds, for example, copolymers of (meth)acrylic acid, benzyl (meth) acrylate, styrene and 2-hydroxyethyl (meth)acrylate, copolymers of (meth)acrylic acid, styrene and α-methystyrene, copolymers of (meth)acrylic acid, N-phenylmaleimide, styrene and benzyl (meth)acrylate, copolymers of (meth)acrylic acid and styrene, copolymers of (meth)acrylic acid and benzyl (meth)acrylate, copolymers of tetrahydrofurfuryl (meth) acrylate, styrene and (meth)acrylic acid and the like.

Examples of the unsaturated compounds having an epoxy group are given below in the formula (V-1)-(V-15);

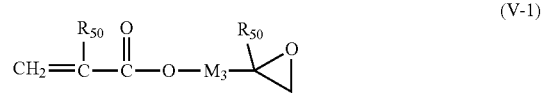
(V-1)

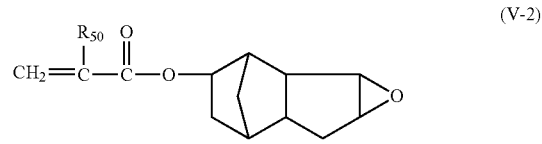
(V-2)

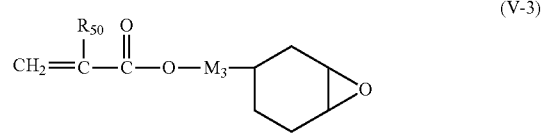
(V-3)

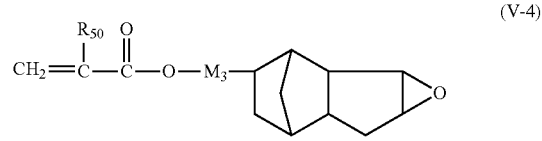
(V-4)

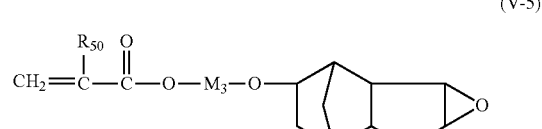
(V-5)

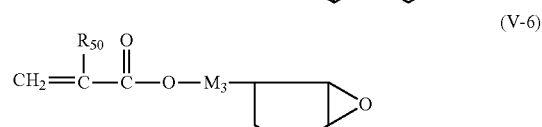
(V-6)

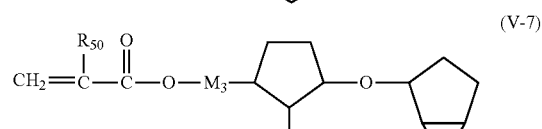
(V-7)

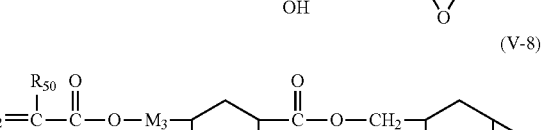
(V-8)

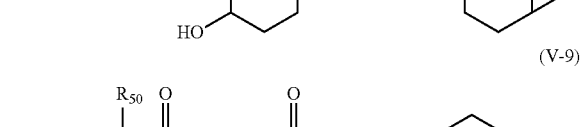
(V-9)

-continued

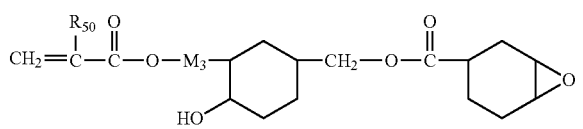
(V-10)

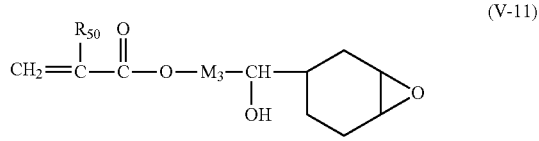
(V-11)

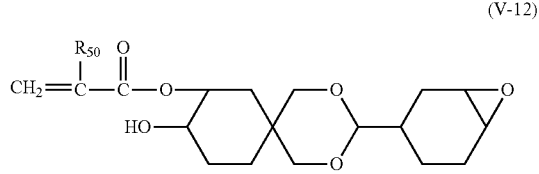
(V-12)

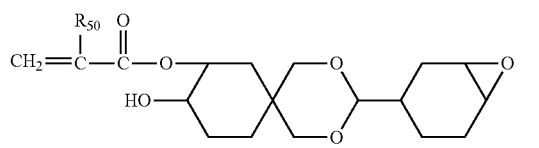
(V-13)

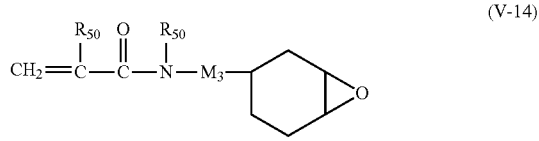
(V-14)

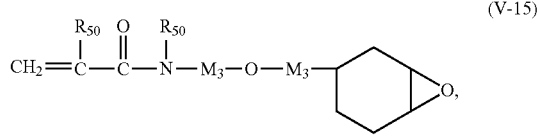
(V-15)

wherein $R_{50}$ is hydrogen or methyl group, $M_3$ is substituted or unsubstituted alkylene having 1 to 10 carbon atoms.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

Concrete examples of the abovementioned compounds are, for example a reaction product of a copolymer of styrene, α-methyl styrene and acrylic acid or a copolymer of methyl methacrylate and acrylic acid with 3,4-epoxycyclohexylmethyl (meth)acrylate.

Other examples are products obtained by addition reaction of an epoxy group containing unsaturated compound to a part of or all of the carboxyl groups of a carboxylic acid group containing polymer followed by further reaction with polybasic acid anhydride (for ex., Ripoxy SPC-3000 provided by Showa Highpolymer).

Unsaturated compounds having a hydroxy group such as 2-hydroxyethyl (meth)acrylate and glycerol mono(meth)acrylate can be used instead of the above mentioned epoxy group containing unsaturated compounds as the reactant for carboxylic acid group containing polymers.

Other examples are half esters of anhydride containing polymers, for example reaction products of a copolymer of maleic anhydride and one or more other polymerizable compounds with (meth)acrylates having an alcoholic hydroxy group such as 2-hydroxyethyl (meth)acrylate or having an epoxy group for example such as the compounds described in the formula (V-1)-(V-15).

Reaction products of polymers having alcoholic hydroxy groups such as copolymers of 2-hydroxyethyl (meth)acrylate, (meth)acrylic acid, benzy methacylate and styrene, with (meth)acrylic acid or (meth)acryl chloride can also be used.

Other examples are reaction products of a polyester with terminal unsaturated groups, which is obtained from the reaction of a dibasic acid anhydride and a compound having at least two epoxy groups followed by further reaction with an unsaturated compound, with a polybasic acid anhydride.

Further examples are resins obtained by the reaction of a saturated or unsaturated polybasic acid anhydride with a reaction product obtained by adding epoxy group containing (meth)acrylic compound to all of the carboxyl groups of a carboxylic acid containing polymer as mentioned above.

Other example is polyimide resin having ethylenically unsaturated groups and at least one carboxyl function. The polyimide binder resin in the present invention can be a polyimide precursor, for example, a poly(amic acid).

Specific examples of alkali developable resins are:

Acrylpolymer type resins such as

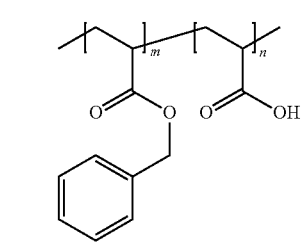

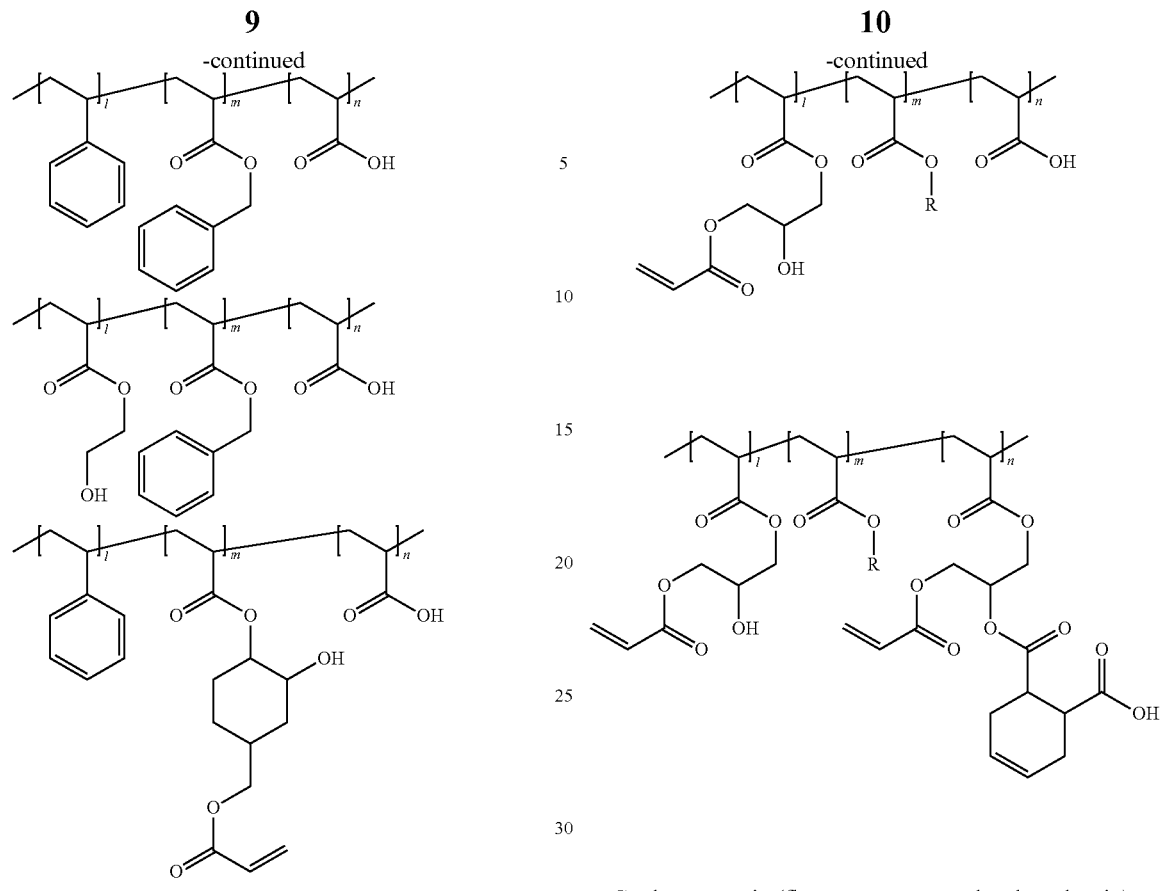
Cardo type resin (fluorene epoxy acrylate based resin)
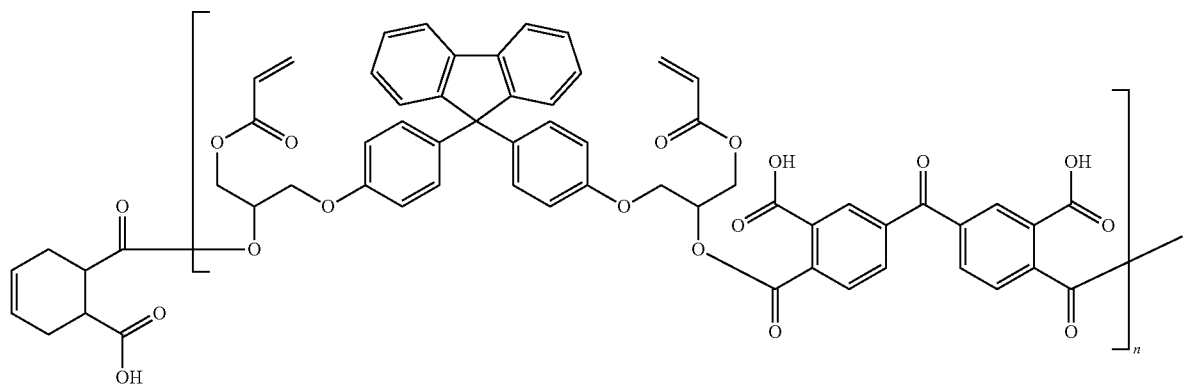
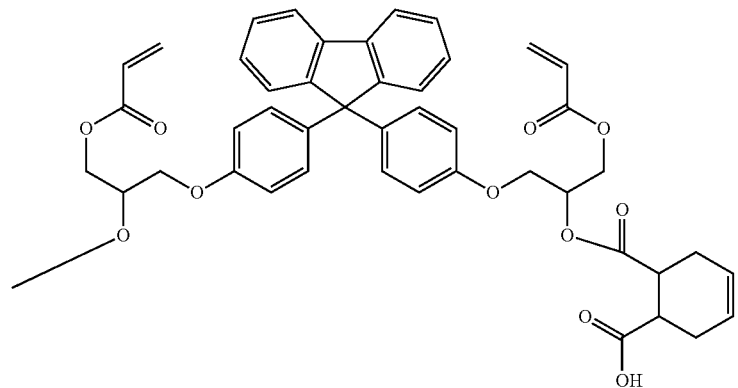

Amount of the Binder Resin

For example, a content of the binder resin may be 2-98%, preferably 5-90% and especially 10-80% by weight based on a total weight of the solid contents in the radically polymerizable composition.

The acrylate monomer refers to an acrylate monomer or oligomer that contains one or more acryloyl or methacryloyl moieties or combinations thereof.

Examples of compounds containing a double bond are (meth)acrylic acid, alkyl, hydroxyalkyl or aminoalkyl (meth) acrylates, for example methyl, ethyl, n-butyl, isobutyl, tert-butyl, n-propyl, isopropyl, n-hexyl, cyclohexyl, 2-ethylhexyl, isobornyl, benzyl, 2-hydroxyethyl, 2-hydroxypropyl, methoxyethyl, ethoxyethyl, glycerol, phenoxyethyl, methoxydiethylene glycol, ethoxydiethylene glycol, polyethylene glycol, polypropylene glycol, glycidyl, N,N-dimethylaminoethyl, and N,N-diethylaminoethyl (meth) acrylates. Other examples are (meth)acrylonitrile, (meth) acrylamide, N-substituted (meth)acrylamides such as N,N-dimethyl (meth)acrylamide, N,N-diethyl (meth)acrylamide, N,N-dibutyl (meth)acrylamide, N-methyl (meth)acrylamide, N-ethyl (meth)acrylamide, N-butyl (meth)acrylamide, and N-(meth)acryloylmorpholine, vinyl esters such as vinyl acetate, vinyl ethers such as isobutyl vinyl ether, styrene, alkyl-, hydroxy- and halostyrenes, N-vinylpyrrolidone, N-vinylcaprolactam, N-vinylacetoamide, N-vinylformamide, vinyl chloride and vinylidene chloride.

Examples of polyunsaturated compounds of relatively high molecular mass (oligomers) are polyesters, polyurethanes, polyethers and polyamides, which contain ethylenically unsaturated carboxylates.

Particularly suitable examples are esters of an ethylenically unsaturated carboxylic acid with a polyol or polyepoxide.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acids are preferred.

Suitable polyols are aromatic, in particular, aliphatic and cycloaliphatic polyols. Examples of aromatic polyols are hydroquinone, 4,4'-dihydroxydiphenyl, 2,2-bis(4-hydroxyphenyl)methane, 2,2-bis(4-hydroxyphenyl)propane, 2,2-bis(4-hydroxyphenyl)hexafluoropropane, 9,9-bis(4-hydroxyphenyl)fluorene, novolacs and resols. Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, triethanolamine, trimethylolethane, trimethylolpropane, pentaerythritol, pentaerythritol monooxalate, dipentaerythritol, ethers of pentaerythritol with ethylene glycol or propylene glycol, ethers of dipentaerythritol with ethylene glycol or propylene glycol, sorbitol, 2,2-bis[4-(2-hydroxyethoxy)phenyl]methane, 2,2-bis[4-(2-hydroxyethoxy)phenyl]propane and 9,9-bis[4-(2-hydroxyethoxy)phenyl]fluorene. Other suitable polyols are polymers and copolymers containing hydroxyl groups in the polymer chain or in side groups, examples being homopolymers or copolymers comprising vinyl alcohol or comprising hydroxyalkyl (meth)acrylates. Further polyols which are suitable are esters and urethanes having hydroxyl end groups.

The polyols may be partially or completely esterified with one unsaturated carboxylic acid or with different unsaturated carboxylic acids, and in partial esters the free hydroxyl groups may be modified, for example etherified or esterified with other carboxylic acids.

Examples of esters based on polyols are trimethylolpropane tri(meth)acrylate, trimethylolpropane tri(acryloyloxypropyl)ether, trimethylolethane tri(meth)acrylate, ethylene glycol di-(meth)acrylate, diethylene glycol di(meth)acrylate, triethylene glycol di(meth)acrylate, tetraethylene glycol di(meth)acrylate, tetramethylene glycol di(meth)acrylate, neopentyl glycol di(meth)acrylate, pentaerythritol di(meth) acrylate, pentaerythritol tri(meth)acrylate, pentaerythritol tetra(meth)acrylate, pentaerythritol tri(meth)acrylate monooxalate, dipentaerythritol di(meth)acrylate, dipentaerythritol tri(meth)acrylate, dipentaerythritol tetra(meth) acrylate, dipentaerythritol penta(meth)acrylate, dipentaerythritol hexa(meth)acrylate, dipentaerythritol penta (meth)acrylate mono(2-hydroxyethyl)ether, tripentaerythritol octa(meth)acrylate, 1,3-butanediol di(meth)acrylate, 1,4-butanediol diitaconate, hexanediol di(meth)acrylate, 1,4-cyclohexanediol di(meth)acrylate, sorbitol tri(meth)acrylate, sorbitol tetra(meth)acrylate, sorbitol penta(meth)acrylate, sorbitol hexa(meth)acrylate, oligoester (meth)acrylates, glycerol di(meth)acrylate and tri(meth)acrylate, di(meth)acrylates of polyethylene glycol with a molecular weight of from 200 to 1500, pentaerythritol diitaconate, dipentaerythritol trisitaconate, dipentaerythritol pentaitaconate, dipentaerythritol hexaitaconate, ethylene glycol diitaconate, propylene glycol diitaconate, 1,3-butanediol diitaconate, 1,4-butanediol diitaconate, tetramethylene glycol diitaconate, sorbitol tetraitaconate, ethylene glycol dicrotonate, tetramethylene glycol dicrotonate, pentaerythritol dicrotonate, ethylene glycol dimaleate, tiethylene glycol dimaleate, pentaerythritol dimaleate, sorbitol tetramaleate, or mixtures thereof.

Other examples are pentaerythritol and dipentaerythritol derivatives shown in the following formula (XII) and (XIII):

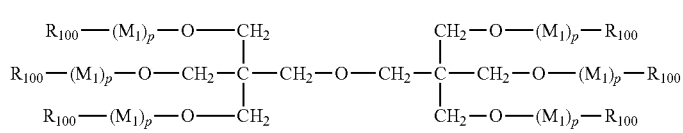

(XII)

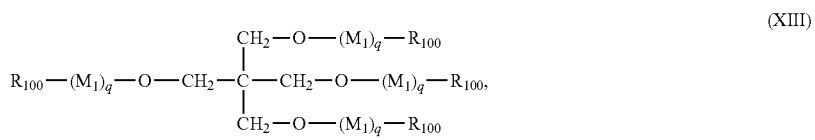

(XIII)

wherein
M$_1$ is —(CH$_2$CH$_2$O)— or —[CH$_2$CH(CH$_3$)O]—,
R$_{100}$ is —COCH=CH$_2$ or —COC(CH$_3$)=CH$_2$,
p is 0 to 6 (total of p: 3-24), and q is 0 to 6 (total of q: 2-16).

Examples of polyepoxides are those based on the above-mentioned polyols and epichlorohydrin. Typical examples are bis(4-glycidyloxyphenyl)methane, 2,2-bis(4-glycidyloxyphenyl)propane, 2,2-bis(4-glycidyloxyphenyl)hexafluoropropane, 9,9-bis(4-glycidyloxyphenyl)fluorene, bis[4-(2-glycidyloxyethoxy)phenyl]methane, 2,2-bis[4-(2-glycidyloxyethoxy)-phenyl]propane, 2,2-bis[4-(2-glycidyloxyethoxy)phenyl]hexafluoropropane, 9,9-bis[4-(2-glycidyloxyethoxy)phenyl]fluorene, bis[4-(2-glycidyloxypropoxy)phenyl]methane, 2,2-bis[4-(2-glycidyloxypropoxy)phenyl]propane, 2,2-bis[4-(2-glycidyloxypropoxy)phenyl]hexafluoropropane, 9,9-bis[4-(2-glycidyloxypropoxy)phenyl]fluorene, glycerol diglycidyl ether and glycidyl ethers of phenol and cresol novolacs.

Typical examples based on polyepoxides are 2,2-bis[4-{(2-hydroxy-3-acryloxy)propoxy}phenyl]propane, 2,2-bis[4-{(2-hydroxy-3-acryloxy)propoxyethoxy}phenyl]propane, 9,9-bis[4-{(2-hydroxy-3-acryloxy)propoxy}phenyl]fluorene, 9,9-bis[4-{(2-hydroxy-3-acryloxy)propoxyethoxy}phenyl]fluorine, glycerol 1,3-diglycerolate diacrylate and reaction products of epoxy resins based on novolacs with (meth)acrylic acid.

Preferred multifunctional (meth)acrylate monomers or oligomers include pentaerythritol tetraacrylate, dipentaerythritol pentaacrylate, dipentaerythritol hexaacrylate, ditrimethylolpropane tetraacrylate, pentaerythritol triacrylate, tris(2-hydroxy ethyl)isocyanurate triacrylate.

Specific examples are:
Dipentaerythritol-hexaacrylate (DPHA)

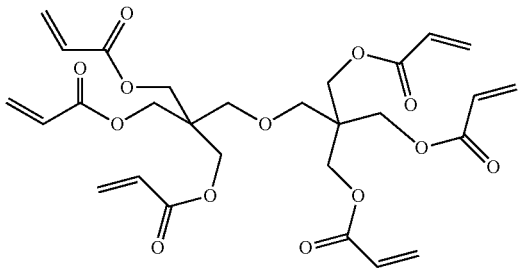 [SMILES: C=CC(=O)OCC(COCC(COC(=O)C=C)(COC(=O)C=C)COC(=O)C=C)(COC(=O)C=C)COC(=O)C=C]

Dipentaerythritol-pentaacrylate (DPPA)

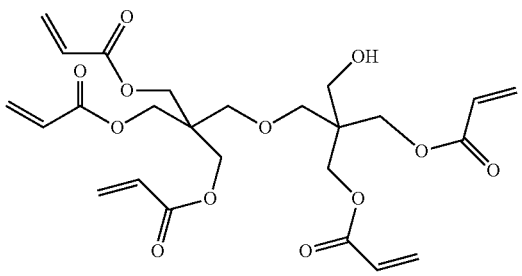 [SMILES: C=CC(=O)OCC(CO)(COCC(COC(=O)C=C)(COC(=O)C=C)COC(=O)C=C)COC(=O)C=C]

Amount of the Acrylate

The amount of acrylate present in the radiation curable composition ranges from about 2% to 80% and preferably from about 5% to 70% based on the whole solid contents of the composition, i.e. the amount of all components without the solvent(s).

Photoinitiators:

The use of the photoinitiator is not critical. The photoinitiator is for example selected from benzophenones, aromatic α-hydroxyketones, benzilketals, aromatic α-aminoketones, phenylglyoxalic acid esters, mono-acylphosphinoxides, bis-acylphosphinoxides, tris-acylphosphinoxides, oximesters derived from aromatic ketones and/or oxime esters of the carbazol type.

Examples of photoinitiators are camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone, thioxanthones, thioxanthone derivatives, polymeric thioxanthones as for example OMNIPOL TX; ketal compounds, as for example benzildimethylketal (IRGACURE® 651); acetophenone, acetophenone derivatives, for example α-hydroxycycloalkyl phenyl ketones or α-hydroxyalkyl phenyl ketones, such as for example 2-hydroxy-2-methyl-1-phenyl-propanone (DAROCURE® 1173), 1-hydroxy-cyclohexyl-phenyl-ketone (IRGACURE®184), 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one (IRGACURE®2959); 2-hydroxy-1-{4-[4-(2-hydroxy-2-methyl-propionyl)-benzyl]-phenyl}-2-methyl-propan-1-one (IRGACURE®127); 2-hydroxy-1-{4-[4-(2-hydroxy-2-methylpropionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane (IRGACURE® 907), (4-morpholinobenzoyl)-1-benzyl-1-dimethylaminopropane (IRGACURE® 369), (4-morpholinobenzoyl)-1-(4-methylbenzyl)-1-dimethylaminopropane (IRGACURE® 379), (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxyethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester (IRGACURE® 754); ketosulfones, e.g. ESACURE KIP 1001 M; oximeesters, e.g. 1,2-octanedione 1-[4-(phenylthio)phenyl]-2-(O-benzoyloxime) (IRGACURE® OXE01), ethanone 1-[9-ethyl-6-(2-methyl-benzoyl)-9H-carbazol-3-yl]-1-(O-acetyloxime) (IRGACURE® OXE02), ethanone 1-[9-ethyl-6-(2-methyl-4-(2,2-dimethyl-1,3-dioxolanyl)methoxybenzoyl)-9H-carbazol-3-yl]-1-(O-acetyloxime), N-Acetoxy-N-{3-[9-ethyl-6-(naphthalene-1-carbonyl)-9H-carbazol-3-yl]-1-methyl-3-acetoxyimino-propyl}-acetamide, 9H-thioxanthene-2-carboxaldehyde 9-oxo-2-(O-acetyloxime), the oxime esters described in WO 07/062,963, WO 07/071,797 and WO 05/080337, peresters, e.g. benzophenone tetracarboxylic peresters as described for example in EP 126541, monoacyl phosphine oxides, e.g. (2,4,6-trimethylbenzoyl)diphenylphosphine oxide (DAROCURE® TPO), ethyl (2,4,6 trimethylbenzoyl phenyl)phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide (IRGACURE®

819), bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole I coinitiators systems, e.g. ortho-chlorohexaphenyl-bisimidazole combined with 2-mercapto-benzthiazole, ferrocenium compounds, or titanocenes, e.g. bis(cyclopentadienyl)-bis(2,6-difluoro-3-pyrryl-phenyl)titanium (IRGACURE®784). Further, borate compounds can be used as coinitiators. As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP provided by Fratelli Lamberti, or oligomeric alpha amino ketones may be employed as well.

Specific Examples are:

IRGACURE® 369 (2-Benzyl-2-(dimethylamino)-1-[4-(4-morpholinyl)phenyl]-1-butanone)

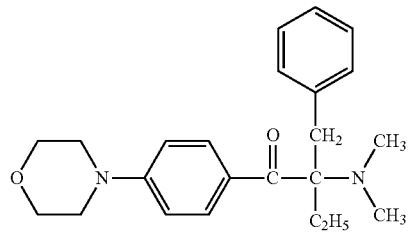 [SMILES: CCC(Cc1ccccc1)(C(=O)c1ccc(N2CCOCC2)cc1)N(C)C]

IRGACURE® 379 (2-(4-Methylbenzyl)-2-(dimethylamino)-1-[4-(4-morpholinyl)phenyl]-1-butanone

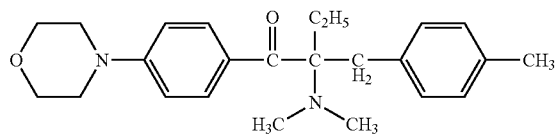 [SMILES: CCC(Cc1ccc(C)cc1)(C(=O)c1ccc(N2CCOCC2)cc1)N(C)C]

Oxime ester 1,2-octanedione, 1-[4-(phenylthio)phenyl]-2-(O-benzoyloxime)

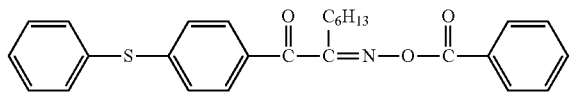

ethanone, 1-[9-ethyl-6-(2-methylbenzoyl)-9H-carbazol-3-yl]-1-(O-acetyloxime)

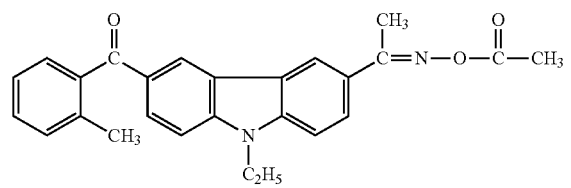 [SMILES: CCn1c2ccc(C(=O)c3ccccc3C)cc2c2cc(C(C)=NOC(C)=O)ccc21]

The Group Ra in Formula I

In a hydroxylamine ester (I) the term acyl with regard to the definition of $R_a$ preferably represents an acyl radical selected from the group consisting of —C(=O)—H, —C(=O)—$C_1$-$C_{32}$alkyl, —C(=O)—$C_2$-$C_{32}$alkenyl, —C(=O)—$C_2$-$C_4$alkenyl-$C_6$-$C_{10}$aryl, —C(=O)—$C_6$-$C_{10}$aryl, —C(=O)—O—$C_1$-$C_6$alkyl, —C(=O)—O—$C_6$-$C_{10}$aryl, —C(=O)—NH—$C_1$-$C_6$alkyl, —C(=O)—NH—$C_6$-$C_{10}$aryl and —C(=O)—N($C_1$-$C_6$alkyl)$_2$; $C_1$-$C_{32}$alkyl in the acyl group $R_a$ is, for example, $C_1$-$C_6$alkyl, e.g. methyl, ethyl, n-propyl or iso-propyl or n-, sec- or tert-butyl or straight-chain or branched pentyl or hexyl, or $C_7$-$C_{19}$alkyl, e.g. straight-chain or branched heptyl, octyl, isooctyl, nonyl, tert-nonyl, decyl or undecyl, or straight-chain $C_{11}$-$C_{19}$alkyl, which together with the —(C=O)— radical forms $C_{14}$-$C_{20}$alkanoyl having an even number of C-atoms, e.g. lauroyl (C12), myristoyl (C14), palmitoyl (C16) or stearoyl (C18).

$C_6$-$C_{10}$Aryl is, for example, carbocyclic monoaryl or diaryl, preferably monoaryl, e.g. phenyl, which may be optionally substituted by suitable substituents, e.g. $C_1$-$C_4$alkyl, e.g. methyl, ethyl or tert-butyl, $C_1$-$C_4$alkoxy, e.g. methoxy or ethoxy, or halogen, e.g. fluorine.

The above-mentioned acyl radical $R_a$ may be substituted on the free valences by suitable substituents, e.g. fluorine or chlorine, and is preferably formyl, acetyl, trifluoroacetyl, pivaloyl, acryloyl, methacryloyl, oleoyl, cinnamoyl, benzoyl, 2,6-xyloyl, tert-butoxycarbonyl, ethylcarbmoyl or phenylcarbamoyl.

Preferred groups Ra are —C(=O)—$C_1$-$C_{32}$alkyl and —C(=O)—$C_6$-$C_{10}$aryl.

The Groups $R_1$-$R_6$ in Formula I $C_1$-$C_6$Alkyl as $R_1$-$R_4$ is preferably $C_1$-$C_4$alkyl, in particular $C_1$-$C_2$alkyl, e.g. methyl or ethyl.

In preferred embodiments, $R_1$-$R_4$ are methyl or ethyl. Alternatively, from one to three substituents $R_1$-$R_4$ are ethyl. The remaining substituents are then methyl.

$R_5$ and $R_6$ are preferably hydrogen, $C_1$-$C_6$alkyl or phenyl.

The Group Rb and Rc in Formula I

In one embodiment Rb is hydrogen and Rc is the substituent —O-G resulting in compounds of the formula IA

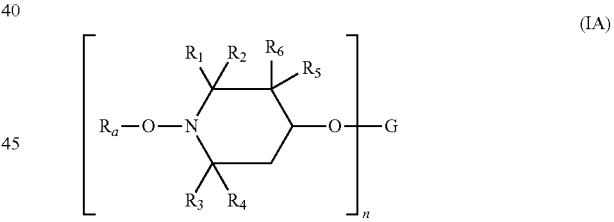

(IA)

Wherein n represents an integer from 1 to 4;
$R_a$, $R_1$-$R_6$ are as defined under formula I; and
G has the following meanings:
When n=1,
G represents hydrogen, $C_1$-$C_{32}$alkyl which may be interrupted by one or more oxygen atoms, 2-cyanoethyl, benzyl, glycidyl, the $C_2$-$C_{32}$acyl radical of an aliphatic carboxylic acid, the $C_2$-$C_{32}$acyl radical of an aliphatic carboxylic acid ($C_2$-$C_{32}$—CO—) wherein the $C_2$-$C_{32}$ alkyl chain may be interrupted by one or more oxygen atoms, $C_7$-$C_{15}$acyl radical of a cycloaliphatic carboxylic acid, the $C_3$-$C_5$acyl radical of an α,β-unsaturated carboxylic acid, or the $C_7$-$C_{15}$acyl radical of an aromatic carboxylic acid, wherein the carboxylic acid groups may be substituted in the aliphatic, cycloaliphatic or aromatic part by 1 to 3-COOZ$^1$ groups, wherein Z$^1$ represents hydrogen, $C_1$-$C_{20}$alkyl, $C_3$-$C_{12}$alkenyl, $C_5$-$C_7$cycloalkyl, phenyl or benzyl; or When n=2, G represents $C_2$-$C_{12}$alkylene, $C_4$-$C_{12}$alkenylene, xylylene, the $C_2$-$C_{36}$acyl radical of an aliphatic dicarboxylic acid, the $C_8$-$C_{14}$acyl radical of a cycloaliphatic or aromatic dicarboxylic acid, or the $C_8$-$C_{14}$acyl radical of an aliphatic, cycloaliphatic or aromatic dicarbamic acid, where the dicarboxylic acid group may be substituted in the aliphatic, cycloaliphatic or aromatic part by 1 or 2-$COOZ^1$ groups, wherein $Z^1$ is as defined above; or When n=3, G represents the trivalent acid radical of an aliphatic, cycloaliphatic or aromatic tricarboxylic acid, wherein the acid radical may be substituted in the aliphatic, cycloaliphatic or aromatic part by the group-$COOZ^1$, wherein $Z^1$ is as defined above, or represents the trivalent acid radical of an aromatic tricarbamic acid or a phosphorus-containing acid or a trivalent silyl radical; or, When n=4, G represents the tetravalent acid radical of an aliphatic, cycloaliphatic or aromatic tetracarboxylic acid.

Definitions Concerning the Formula IA

G defined as $C_1$-$C_{32}$Alkyl may, for example, have the meanings indicated above for alkyl and may additionally be, for example, n-tridecyl, n-tetradecyl, n-hexadecyl or n-octadecyl.

A monovalent acyl radical of a carboxylic acid as G may be, for example, the acyl radical of acetic acid, hexanoic acid, stearic acid, acrylic acid, methacrylic acid, benzoic acid or β-(3,5-di-tert-butyl-4-hydroxyphenyl)propionic acid; preferably the acyl radical of stearic acid, acrylic acid or methacrylic acid.

A monovalent silyl radical G may be, for example, a radical —$(C_nH_{2n})$—$Si(Z')_2Z''$, where n is an integer from 2 to 5 and $Z'$ and $Z''$ are each, independently of one another $C_1$-$C_4$alkyl or $C_1$-$C_4$alkoxy.

A divalent acid radical of a dicarboxylic acid as G may be, for example, the acid radical of malonic acid, succinic acid, glutaric acid, adipic acid, suberic acid, sebacic acid, maleic acid, itaconic acid, phthalic acid, dibutylmalonic acid, dibenzylmalonic acid, butyl(3,5-di-tert-butyl-4-hydroxybenzyl)malonic acid or bicycloheptenedicarboxylic acid.

A trivalent radical of a tricarboxylic acid as G may be, for example, the acid radical of trimellitic acid, citric acid or nitrilotriacetic acid.

A tetravalent radical of a tetracarboxylic acid as G may be, for example, the tetravalent acid radical of butane-1,2,3,4-tetracarboxylic acid or of pyromellitic acid.

A divalent radical of a dicarbamic acid as G may be, for example, the hexamethylenedicarbamic acid radical or the 2,4-toluoylenedicarbamic acid radical.

Preferred Formula IA

According to a preferred embodiment n represents in a compound (IA) 1 or 2, $R_1$-$R_4$ are each independently methyl or ethyl, $R_5$ and $R_6$ are each independently hydrogen or methyl, $R_a$ represents —C(=O)—$C_1$-$C_{32}$alkyl or —C(=O)-phenyl G represents the $C_2$-$C_{32}$acyl radical of an aliphatic carboxylic acid ($C_2$-$C_{32}$—CO—); the $C_2$-$C_{32}$acyl radical of an aliphatic carboxylic acid ($C_2$-$C_{32}$—CO—) wherein the $C_2$-$C_{32}$ alkyl chain may be interrupted by one or more oxygen atoms or the $C_4$-$C_{12}$acyl radical of an aliphatic dicarboxylic acid.

In one embodiment Rb is hydrogen and Rc is —$NG1G2$ resulting in compounds of the formula IB

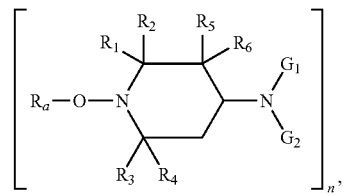

Wherein n represents an integer from 1 to 2;

$R_a$, $R_1$-$R_6$ are as defined under formula I; and $G^1$ represents hydrogen, $C_1$-$C_{12}$alkyl, $C_2$-$C_5$hydroxyalkyl, $C_5$-$C_7$cycloalkyl, $C_7$-$C_8$aralkyl, $C_2$-$C_{18}$alkanoyl, $C_3$-$C_5$alkenoyl or benzoyl or a group:

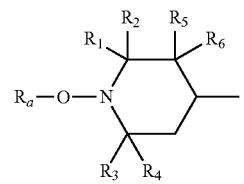

Wherein $R_a$ and $R_1$-$R_6$ are as defined under formula I and $G^2$ has the following meanings:

When n=1, $G^2$ represents hydrogen, $C_1$-$C_{18}$alkyl, $C_3$-$C_8$alkenyl, $C_5$-$C_7$cycloalkyl, $C_1$-$C_4$alkyl, $C_1$-$C_4$alkyl substituted by hydroxy, cyano, alkoxycarbonyl or carbamide, glycidyl or the groups —$CH_2$—CH(OH)—Z or CONH—Z, wherein Z is hydrogen, methyl or phenyl; or $G^1$ and $G^2$ together represent the bivalent radical of an aliphatic, cycloaliphatic or aromatic 1,2-dicarboxylic acid or 1,3-dicarboxylic acid;

When n=2, $G^2$ represents hydrogen, $C_2$-$C_{12}$alkylene, $C_6$-$C_{12}$arylene, xylylene or the —$CH_2CH(OH)$—$CH_2$— or —$CH_2$—CH(OH)—$CH_2$—O-D-O— groups, wherein D represents $C_2$-$C_{10}$alkylene, $C_6$-$C_{15}$arylene or $C_6$-$C_{12}$cycloalkylene; or, provided that $G^1$ is other than alkanoyl, alkenoyl or benzoyl, $G^2$ additionally represents 1-oxo-$C_2$-$C_{12}$alkylene, the bivalent radical of an aliphatic, cycloaliphatic or aromatic dicarboxylic acid or dicarbamic acid or the —CO— group.

Definitions Concerning the Formula IB $C_1$-$C_{12}$Alkyl and $C_1$-$C_{18}$alkyl substituents are as defined above under the formula (IA).

$C_5$-$C_7$Cycloalkyl is preferably cyclohexyl.

A $C_7$-$C_8$aralkyl group $G^1$ is preferably 2-phenylethyl or benzyl.

A $C_2$-$C_5$hydroxyalkyl group $G^1$ is preferably 2-hydroxyethyl or 2- or 3-hydroxypropyl.

A $C_2$-$C_{18}$alkanoyl group $G^1$ may be, for example, propionyl, butyryl, octanoyl, dodecanoyl, hexadecanoyl, octadecanoyl, preferably acetyl.

A $C_3$-$C_5$alkenoyl group $G^1$ is preferably acryloyl.

A $C_2$-$C_8$alkenyl group $G^2$ may be, for example, allyl, methallyl, 2-butenyl, 2-pentenyl, 2-hexenyl or 2-octenyl.

A hydroxy-, cyano-, alkoxycarbonyl- or carbamido-substituted $C_1$-$C_4$alkyl group $G^2$ may be, for example, 2-hydroxyethyl, 2-hydroxypropyl, 2-cyanoethyl, methoxycarbonylmethyl, 2-ethoxycarbonylethyl, 2-aminocarbonylpropyl or 2-(dimethylaminocarbonyl)ethyl.

A $C_2$-$C_{12}$alkylene group $G^2$ may be, for example, ethylene, propylene, 2,2-dimethylpropylene, tetramethylene, hexamethylene, octamethylene, decamethylene or dodecamethylene.

A $C_6$-$C_{15}$arylene group $G^2$ may be, for example, o-, m- or p-phenylene, 1,4-naphthylene or 4,4'-biphenylene.

A $C_6$-$C_{12}$-cycloalkylene group $G^2$ is preferably cyclohexylene.

In one embodiment $R_b$ and $R_c$ form a ring resulting in compounds of the formula IC $$\left[\begin{array}{c} R_1 \quad R_2 \quad R_5 \\ R_a-O-N \qquad \qquad R_6 \\ \qquad\qquad\qquad O \\ \qquad\qquad\qquad \quad G^3, \\ \qquad\qquad\qquad O \\ R_3 \quad R_4 \end{array}\right]_n \quad (IC)$$

wherein
$R_a$, $R_1$-$R_6$ are as defined under formula I,
$G^3$ has the following meanings:
When n is 1
$G^3$ is $C_2$-$C_8$alkylene, $C_2$-$C_8$hydroxyalkylene, $C_2$-$C_8$acyloxyalkylene or a group <img: structure showing C1-C4-alkyl backbone with -O-C(=O)-Ra' and two binding sites *> wherein
Ra' is $C_1$-$C_{32}$ alkyl or $C_1$-$C_{32}$alkyl interrupted by one or more oxygen or $C_1$-$C_{32}$alkyl substituted by hydroxyl, acyloxyl, or carboxylate groups
and * are the binding sites
When n is 2
$G^3$ is the group (—$CH_2$)$_2$C(—$CH_2$—)$_2$ Definitions Concerning the Formula IC A $C_2$-$C_8$alkylene or $C_2$-$C_8$hydroxyalkylene group $G^3$ may be, for example, ethylene, 1-methylethylene, propylene, 2-ethylpropylene or 2-ethyl-2-hydroxymethylpropylene.

A $C_2$-$C_8$-acyloxyalkylene group $G^3$ may be, for example, 2-ethyl-2-acetoxymethylpropylene.

A $C_1$-$C_{32}$alkyl group Ra' interrupted by one or more oxygen is derived from a polyethylene or polypropylene glycol ether. Examples are C1 C6 ethers such as methylether, ethylether, propylether, butylether. A specific example is triethylene glycol mono-n-butylether.

A $C_1$-$C_{32}$alkyl group Ra' substituted by hydroxy denotes for example the following groups: —CH(OH)CH$_3$, —CH$_2$CH(OH)CH$_3$, —CH$_2$CH(CH$_3$)CH$_2$OH, —(CH$_2$)$_{2\text{-}18}$OH or —CH$_2$C[(CH$_3$)]$_2$—CH$_2$OH.

Preferred hydroxylamine esters of the formula IC are NOR2, NOR3, NOR5, NOR9 and NOR14 described in Example 2.

In one embodiment Rb and Rc form a ring resulting in compounds of the formula ID-1H $$\left[\begin{array}{c} R_1 \quad R_2 \quad R_5 \quad R_6 \qquad G^4 \\ \qquad\qquad\qquad\qquad\qquad N \qquad O \\ R_a-O-N \qquad\qquad\qquad\qquad \\ \qquad\qquad\qquad\qquad\qquad N-G^5, \\ R_3 \quad R_4 \qquad\qquad\qquad\qquad O \end{array}\right]_n \quad (ID)$$

$$\left[\begin{array}{c} R_1 \quad R_2 \quad R_5 \quad R_6 \qquad T_1 \\ \qquad\qquad\qquad\qquad\qquad O-T_2, \text{ or} \\ R_a-O-N \qquad\qquad\qquad\qquad \\ \qquad\qquad\qquad\qquad\qquad N \qquad O \\ R_3 \quad R_4 \qquad\qquad\qquad\qquad H \end{array}\right]_n \quad (IE)$$

$$\left[\begin{array}{c} R_1 \quad R_2 \quad R_5 \quad R_6 \qquad T_1 \\ \qquad\qquad\qquad\qquad\qquad O-T_2 \\ R_a-O-N \qquad\qquad\qquad\qquad \\ \qquad\qquad\qquad\qquad\qquad N-G^5, \\ R_3 \quad R_4 \qquad\qquad\qquad O \end{array}\right]_n \quad (IF)$$

wherein
$R_a$, $R_1$-$R_6$ are as defined under formula I,
n represents 1 or 2;
$G^4$ represent hydrogen, $C_1$-$C_{12}$alkyl, allyl, benzyl, glycidyl or $C_2$-$C_6$alkoxyalkyl; and
$G^5$ has the following meanings:
When n=1,
$G^5$ represents hydrogen, $C_1$-$C_{12}$alkyl, $C_3$-$C_5$alkenyl, $C_7$-$C_9$aralkyl, $C_5$-$C_7$cycloalkyl, $C_2$-$C_4$hydroxyalkyl, $C_2$-$C_6$alkoxyalkyl, $C_6$-$C_{10}$aryl, glycidyl or the groups —(CH$_2$)$_p$—COO-Q or —(CH$_2$)$_p$—O—CO-Q, wherein p represents 1 or 2 and Q represents $C_1$-$C_4$alkyl or phenyl; or
When n=2,
$G^5$ represents $C_2$-$C_{12}$alkylene, $C_4$-$C_{12}$alkenylene, $C_6$-$C_{12}$arylene, the group

—CH$_2$—CH(OH)—CH$_2$—O-D-O—CH$_2$—CH(OH)—CH$_2$—,

Wherein D represents $C_2$-$C_{10}$alkylene, $C_6$-$C_{15}$arylene or $C_6$-$C_{12}$-cycloalkylene, or the group

—CH$_2$CH(OZ')CH$_2$—(OCH$_2$—CH(OZ')CH$_2$)$_2$—,

Wherein Z' represents hydrogen, $C_1$-$C_i$salkyl, allyl, benzyl, $C_2$-$C_{12}$alkanoyl or benzoyl,
$T^1$ and $T^2$ each represent, independently of one another, hydrogen, $C_1$-$C_{18}$alkyl, $C_6$-$C_{10}$aryl or $C_7$-$C_9$aralkyl, each of which may be substituted by halogen or $C_1$-$C_4$alkyl, or
$T^1$ and $T^2$ together with the carbon atom connecting them form a $C_5$-$C_{14}$cycloalkane ring.

According to another preferred embodiment of the invention, the hydroxylamine ester (I) of component a) is selected from a compound of the formula:

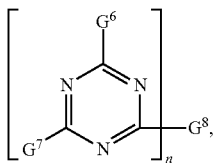

(IG)

Wherein n=1 or 2 and $G^6$ represents the group:

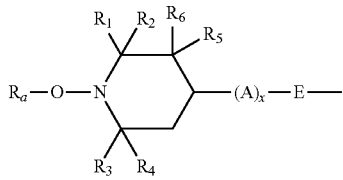

$R_a$, $R_1$-$R_6$ are as defined under formula I,

E represents —O— or —$NG^1$—;

A represents $C_2$-$C_6$alkylene or —$(CH_2)_3$—O—;

x is either 0 or 1;

$G^1$ represents hydrogen, $C_1$-$C_{12}$alkyl, $C_2$-$C_5$hydroxyalkyl or $C_5$-$C_7$cycloalkyl;

$G^7$ is identical with $G^6$ or represents one of the groups —$NG^9G^{10}$, —$OG^{11}$, —$NHCH_2OG^{11}$ or —$N(CH_2OG^{11})_2$;

When n=1, $G^8$ is identical with $G^6$ or $G^7$; and,

When n=2, $G^8$ represents the group -E-B-E-, wherein B represents $C_2$-$C_8$alkylene or $C_2$-$C_8$alkylene interrupted by 1 or 2 —$NG^9$- groups, and $G^9$ represents $C_1$-$C_{12}$alkyl, cyclohexyl, benzyl or $C_1$-$C_4$hydroxyalkyl or the groups:

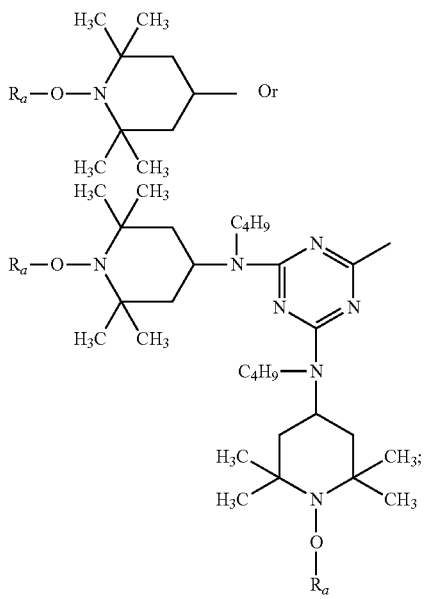

$G^{10}$ represents $C_1$-$C_{12}$alkyl, cyclohexyl, benzyl or $C_1$-$C_4$-hydroxyalkyl; and $G^{11}$ represents hydrogen, $C_1$-$C_{12}$alkyl or phenyl; and $G^9$ and $G^{10}$ together represent $C_4$-$C_5$alkylene or $C_4$-$C_5$oxaalkylene.

According to another alternative embodiment of the invention the hydroxylamine ester (I) of component a) is selected from a compound of the formula:

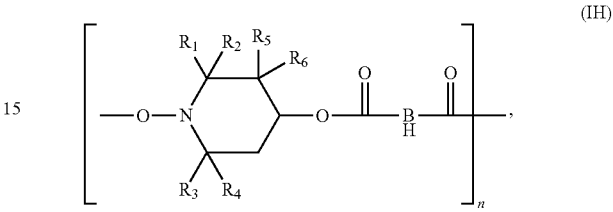

(IH)

Wherein n represents an integer greater than two and $R_a$, $R_1$-$R_6$ are as defined under formula I, and B is a bivalent substituent.

Preparation

The hydroxylamine esters (I) are known or can be prepared by known methods, e.g. by acylation of the corresponding >N—OH compound in a customary esterification reaction with an acid $R_a$—OH that introduces the group $R_a$ and corresponds to an acyl group selected, for example, from the group consisting of —C(=O)—H, —C(=O)—$C_1$-$C_{19}$alkyl, —C(=O)—$C_2$-$C_{19}$alkenyl, —C(=O)—$C_2$-$C_4$alkenyl-$C_6$-$C_{10}$aryl, —C(=O)—$C_6$-$C_{10}$aryl, —C(=O)—O—$C_1$-$C_6$alkyl, —C(=O)—O—$C_6$-$C_{10}$aryl, —C(=O)—NH—$C_1$-$C_6$alkyl, —C(=O)—NH—$C_6$-$C_{10}$aryl and —C(=O)—N($C_1$-$C_6$alkyl)$_2$, or a reactive functional derivative thereof, e.g. the acid halide $R_a$—X, e.g. the acid chloride, or anhydride, e.g. ($R_a$)$_2$O. The hydroxylamine esters (I) and methods for their preparation are described in WO 01/90113.

Best Mode

According to a most preferred embodiment the hydroxylamine ester (I) is selected from the group consisting of sterically hindered amine derivatives of the formula:

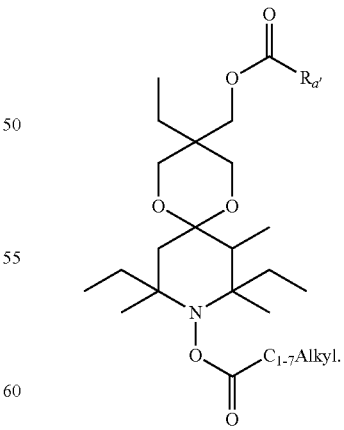

wherein $R_{a'}$ is $C_1$-$C_{21}$ alkyl or $C_1$-$C_{21}$alkyl interrupted by one or more oxygen.

Examples of best mode candidates are the following and the NOR compounds described in Example 2:

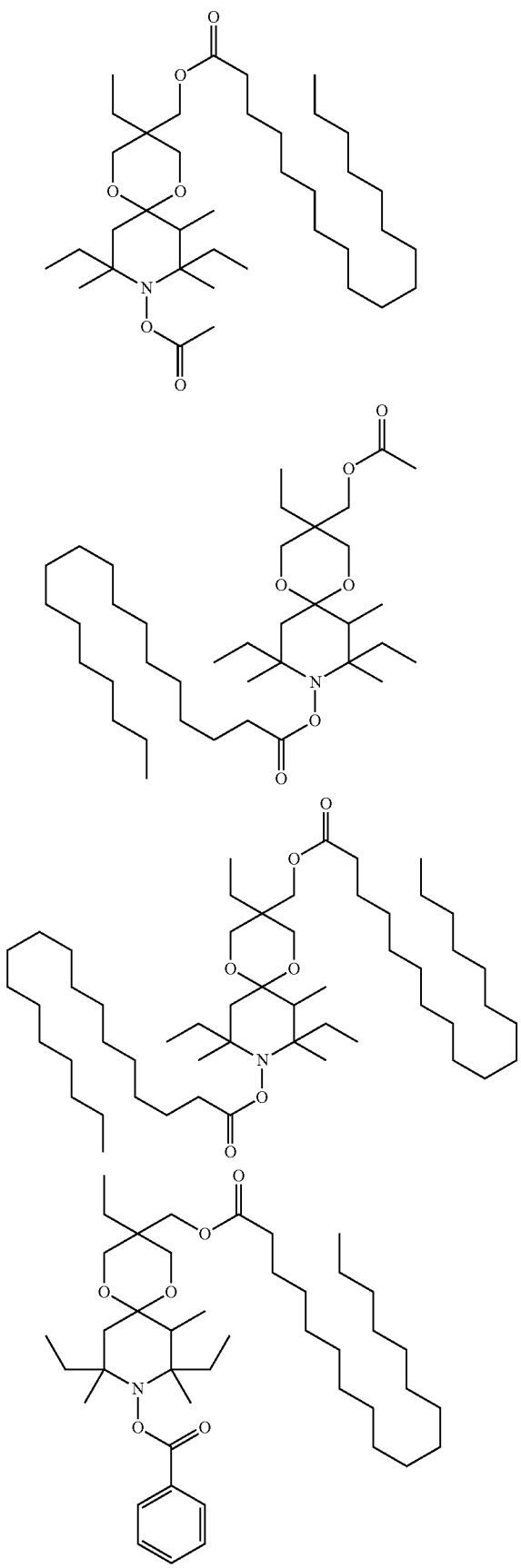
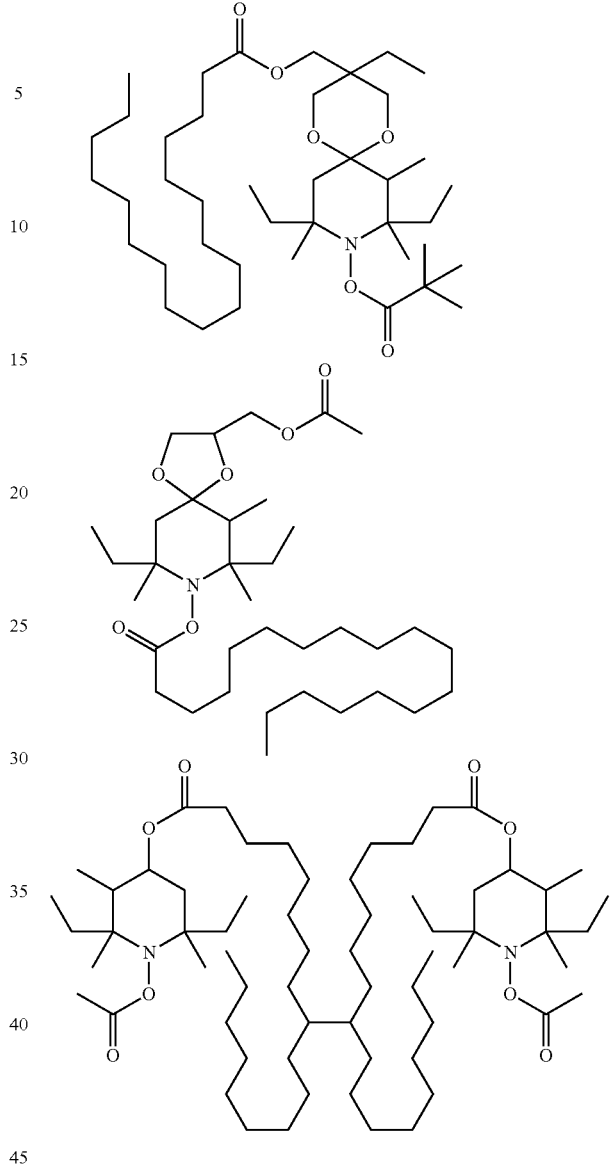
Novel Compounds
Some compounds of the formula I A and of the formula IC are novel.
Thus the invention further relates to novel compounds of the formula IC'
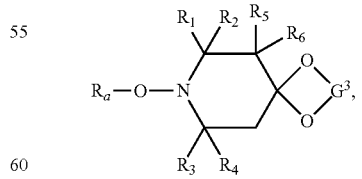
(IC')
wherein
$R_1$-$R_4$ each represent $C_1$-$C_6$alkyl; and
$R_5$ and $R_6$ each represent independently of one another hydrogen, $C_1$-$C_6$alkyl or $C_6$-$C_{10}$aryl; or $R_5$ and $R_6$ together represent oxygen, Ra is an acyl radical selected from —C(=O)—H, —C(=O)—C$_1$-C$_{32}$alkyl, —C(=O)—C$_2$-C$_{32}$alkenyl, —C(=O)—C$_2$-C$_4$alkylene-C$_6$-C$_{10}$aryl, C(=O)—C$_2$-C$_4$alkylene-C(=O)—C$_1$-C$_{32}$alkyl, —C(=O)—C$_6$-C$_{10}$aryl, —C(=O)—O—C$_1$-C$_{32}$alkyl, —C(=O)—O-benzyl, —C(=O)—O—C$_6$-C$_{10}$aryl, —C(=O)—NH—C$_1$-C$_{32}$alkyl, —C(=O)—NH—C$_6$-C$_{10}$aryl and —C(=O)—N(C$_1$-C$_{32}$alkyl)$_2$, wherein C$_1$-C$_{32}$alkyl and C$_6$-C$_{10}$aryl may be optionally interrupted by one or more O or C=O and/or substituted by one or more halogen, OR$_9$, COOR$_9$, CONR$_9$R$_{10}$, phenyl or phenyl substituted by halogen, C$_1$-C$_{32}$alkyl, C$_1$-C$_4$haloalkyl, SR$_9$, OR$_9$, or NR$_9$R$_{10}$; wherein R$_9$ and R$_{10}$ independently of one another are hydrogen or unsubstituted or substituted C$_1$-C$_{32}$alkyl, C$_6$-C$_{10}$aryl, C$_4$-C$_{10}$heteroaryl, C$_7$-C$_{20}$aralkyl or C$_4$-C$_{20}$cycloalkyl, whereby the alkyl and cycloalkyl are uninterrupted or interrupted by O;

G$^3$ is C$_2$-C$_8$alkylene substituted by one or more OR$_7$, C$_2$-C$_8$hydroxyalkylene substituted by one or more OR$_8$; 1,2-phenylene or 1-methylene-2-phenyl, each of which optionally is substituted by one or more C$_1$-C$_{20}$alkyl, halogen, phenyl, OR$_8$, COOR$_9$, CONR$_9$R$_{10}$ or C$_1$-C$_{20}$alkyl interrupted by one or more O and/or substituted by halogen or OR$_8$; with R$_7$ is C$_1$-C$_{32}$alkyl, C$_4$-C$_{20}$cycloalkyl, —C(=O)—C$_4$-C$_{20}$cycloalkyl, —C(=O)—C$_2$-C$_{32}$alkenyl, —C(=O)—C$_2$-C$_4$alkenyl-C$_6$-C$_{10}$aryl, —C(=O)—(CH$_2$)$_{1-4}$—C(=O)—C$_1$-C$_{32}$alkyl, —C(=O)—C$_6$-C$_{10}$aryl, —C(=O)-benzyl, —C(=O)—O—C$_1$-C$_{32}$alkyl, —C(=O)—O—C$_6$-C$_{10}$aryl, —C(=O)—NH—C$_1$-C$_{32}$alkyl, —C(=O)—NH—C$_6$-C$_{10}$aryl —C(=O)—N(C$_1$-C$_{32}$alkyl)$_2$ or —C(=S)—NH—C$_6$-C$_{10}$aryl, wherein C$_1$-C$_{32}$alkyl, C$_4$-C$_{20}$cycloalkyl and C$_6$-C$_{10}$aryl may be optionally substituted by one or more halogen, OR$_8$, COOR$_8$, CONR$_8$R$_9$, phenyl or phenyl substituted by halogen, C$_1$-C$_{32}$alkyl, C$_1$-C$_4$haloalkyl, SR$_8$, OR$_8$, or NR$_8$R$_9$ and/or C$_1$-C$_{32}$alkyl and C$_4$-C$_{20}$cycloalkyl may be interrupted by one or more O or C=O; or —C(=O)—C$_1$-C$_{32}$alkyl, which is interrupted by one or more O or C=O and/or substituted by one or more halogen, OR$_8$, COOR$_8$, CONR$_8$R$_9$, phenyl or phenyl substituted by halogen, C$_1$-C$_{32}$alkyl, C$_1$-C$_4$haloalkyl, SR$_8$, OR$_8$, or NR$_8$R$_9$;

R$_8$ is hydrogen, C$_1$-C$_{32}$alkyl, C$_4$-C$_{20}$cycloalkyl, —C(=O)—C$_1$-C$_{32}$alkyl, —C(=O)—C$_4$-C$_{20}$cycloalkyl, —C(=O)—C$_2$-C$_{32}$alkenyl, —C(=O)—C$_2$-C$_4$alkenyl-C$_6$-C$_{10}$aryl, —C(=O)—C$_6$-C$_{10}$aryl, —C(=O)—O—C$_1$-C$_{32}$alkyl, —C(=O)—O—C$_6$-C$_{10}$aryl, —C(=O)—NH—C$_1$-C$_{32}$alkyl, —C(=O)—NH—C$_6$-C$_{10}$aryl —C(=O)—N(C$_1$-C$_{32}$alkyl)$_2$ or —C(=S)—NH—C$_6$-C$_{10}$aryl, wherein C$_1$-C$_{32}$alkyl, C$_4$-C$_{20}$cycloalkyl and C$_6$-C$_{10}$aryl may be optionally substituted by one or more halogen, OR$_9$, COOR$_9$, CONR$_9$R$_{10}$, phenyl or phenyl substituted by halogen, C$_1$-C$_{32}$alkyl, C$_1$-C$_4$haloalkyl, SR$_9$, OR$_9$, or NR$_9$R$_{10}$ and/or C$_1$-C$_{32}$alkyl and C$_4$-C$_{20}$cycloalkyl may be interrupted by one or more O or C=O;

R$_9$ and R$_{10}$ independently of one another are hydrogen or unsubstituted or substituted C$_1$-C$_{32}$alkyl, C$_6$-C$_{10}$aryl, C$_4$-C$_{10}$heteroaryl, C$_7$-C$_{20}$aralkyl or C$_4$-C$_{20}$cycloalkyl, whereby the alkyl and cycloalkyl are uninterrupted or interrupted by O.

The group Ra in formula IC' is preferably an acyl radical selected from —C(=O)—C$_1$-C$_{32}$alkyl, —C(=O)—C$_2$-C$_4$alkylene-C(=O)—C$_1$-C$_{32}$alkyl, —C(=O)-phenyl or —C(=O)-phenyl substituted by methoxy, —C(=O)—O—C$_1$-C$_{32}$alkyl, —C(=O)—O-benzyl, —C(=O)—NH—C$_1$-C$_{32}$alkyl, —C(=O)—NH-phenyl.

The definition of the residue G3 "C$_2$-C$_8$alkylene substituted by one or more OR$_7$" means linear or branched alkylene

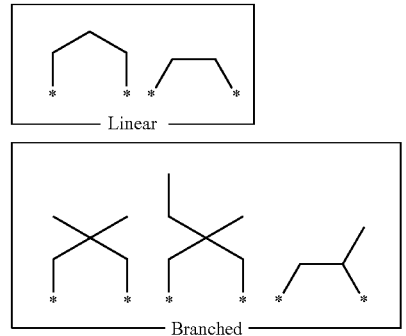

Preferably C$_2$-C$_3$ alkylene. The branching point is preferably at the same C-atom.

In one embodiment
G$^3$ a group wherein

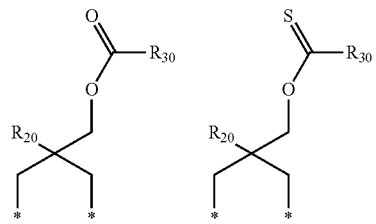

R$_{20}$ is C$_{1-6}$alkyl, preferably methyl or ethyl or R$_{20}$ is a group C$_1$-C$_{20}$alkyl-COO—CH$_2$—

R$_{30}$ is C$_1$-C$_{32}$alkyl interrupted by one or more oxygen or C$_4$-C$_{20}$cycloalkyl, C$_2$-C$_{32}$alkenyl, —C$_2$-C$_4$alkylene-C$_6$-C$_{10}$aryl, —(CH$_2$)$_{1-4}$—C(=O)—C$_1$-C$_{32}$alkyl, C$_6$-C$_{10}$aryl, —O—C$_1$-C$_{32}$alkyl, —O—C$_6$-C$_{10}$aryl, —O-benzyl, —NH—C$_1$-C$_{32}$alkyl, —NH—C$_6$-C$_{10}$aryl, —N(C$_1$-C$_{32}$alkyl)$_2$ or —NH—C$_6$-C$_{10}$aryl; wherein the C$_6$-C$_{10}$aryl is unsubstituted or substituted by one or more halogen atoms or by OR$_8$ wherein R$_8$ is hydrogen, C$_1$-C$_{32}$alkyl, C$_4$-C$_{20}$cycloalkyl, and wherein C$_1$-C$_{32}$alkyl, C$_4$-C$_{20}$cycloalkyl and C$_6$-C$_{10}$aryl may be optionally substituted by one or more halogen, OR$_9$, COOR$_9$, CONR$_9$R$_{10}$, phenyl or phenyl substituted by halogen, C$_1$-C$_{32}$alkyl, C$_1$-C$_4$haloalkyl, SR$_9$, OR$_9$, or NR$_9$R$_{10}$ and/or C$_1$-C$_{32}$alkyl and C$_4$-C$_{20}$cycloalkyl may be interrupted by one or more O or C=O; R$_9$ and R$_{10}$ independently of one another are hydrogen or unsubstituted or substituted C$_1$-C$_{32}$alkyl, C$_6$-C$_{10}$aryl, C$_4$-C$_{10}$heteroaryl, C$_7$-C$_{20}$aralkyl or C$_4$-C$_{20}$cycloalkyl, whereby the alkyl and cycloalkyl are uninterrupted or interrupted by O.

The aryl group in the residue R$_{30}$ is preferably a phenyl group. Substituted phenyl groups are for example halogen substituted phenyl groups, e.g. fluorine substituted having 1 to 5 fluorine atoms. Substituted phenyl groups may also be alkoxy substituted phenyl groups, e.g. methoxy.

The residue R$_{30}$ is preferably C$_1$-C$_{32}$alkyl interrupted by one or more oxygen phenyl or benzyl or phenyl substituted by one or more halogen atoms or is substituted by OR$_8$, —(CH$_2$)$_{1-4}$—C(=O)—C$_1$-C$_{32}$alkyl or O-benzyl, —O—C$_1$-C$_{32}$alkyl, —NH—C$_1$-C$_{32}$alkyl, —NH-phenyl.

In one embodiment G$^3$ a group

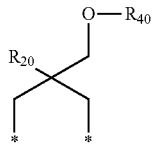

wherein or R$_{20}$ is a group C$_1$-C$_{20}$alkyl-COO—CH$_2$—

R$_{40}$ is C$_1$-C$_{32}$ alkyl being substituted by one or more than one acyloxy group.

The acyloxy group in R$_{40}$ is e.g. an CH$_3$—COO-group or —CH$_2$—C((CH$_2$)—O—CO—CH$_3$)$_3$.

In one embodiment G$^3$ is a group

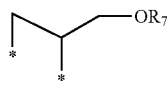

wherein

R$_7$ is C$_1$-C$_{32}$alkyl, C$_4$-C$_{20}$cycloalkyl, —C(=O)—C$_4$-C$_{20}$cycloalkyl, —C(=O)—C$_2$-C$_{32}$alkenyl, —C(=O)—C$_2$-C$_4$alkenyl-C$_6$-C$_{10}$aryl, —C(=O)—(CH$_2$)$_{1-4}$—C(=O)—C$_1$-C$_{32}$alkyl, —C(=O)—C$_6$-C$_{10}$aryl, —C(=O)-benzyl, —C(=O)—O—C$_1$-C$_{32}$alkyl, —C(=O)—O—C$_6$-C$_{10}$aryl, —C(=O)—NH—C$_1$-C$_{32}$alkyl, —C(=O)—NH—C$_6$-C$_{10}$aryl —C(=O)—N(C$_1$-C$_{32}$alkyl)$_2$ or —C(=S)—NH—C$_6$-C$_{10}$aryl, wherein C$_1$-C$_{32}$alkyl, C$_4$-C$_{20}$cycloalkyl and C$_6$-C$_{10}$aryl may be optionally substituted by one or more halogen, OR$_8$, COOR$_8$, CONR$_8$R$_9$, phenyl or phenyl substituted by halogen, C$_1$-C$_{32}$alkyl, C$_1$-C$_4$haloalkyl, SR$_8$, OR$_8$, or NR$_8$R$_9$ and/or C$_1$-C$_{32}$alkyl and C$_4$-C$_{20}$cycloalkyl may be interrupted by one or more O or C=O; or —C(=O)—C$_1$-C$_{32}$alkyl, which is interrupted by one or more O or C=O and/or substituted by one or more halogen, OR$_8$, COOR$_8$, CONR$_8$R$_9$, phenyl or phenyl substituted by halogen, C$_1$-C$_{32}$alkyl, C$_1$-C$_4$haloalkyl, SR$_8$, OR$_8$, or NR$_8$R$_9$.

In one embodiment G$^3$ is

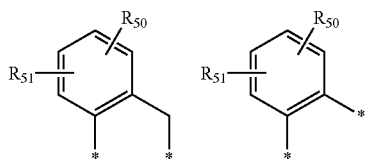

Wherein R$_{50}$ and R$_{51}$ independently of one another are C$_1$-C$_{20}$alkyl, halogen, C$_1$-C$_{20}$alkoxy, —OCOC$_1$-C$_{20}$alkyl, —COOC$_1$-C$_{20}$alkyl, —CONHC$_1$-C$_{20}$alkyl, or —CONH$_2$.

Examples of new compounds are:

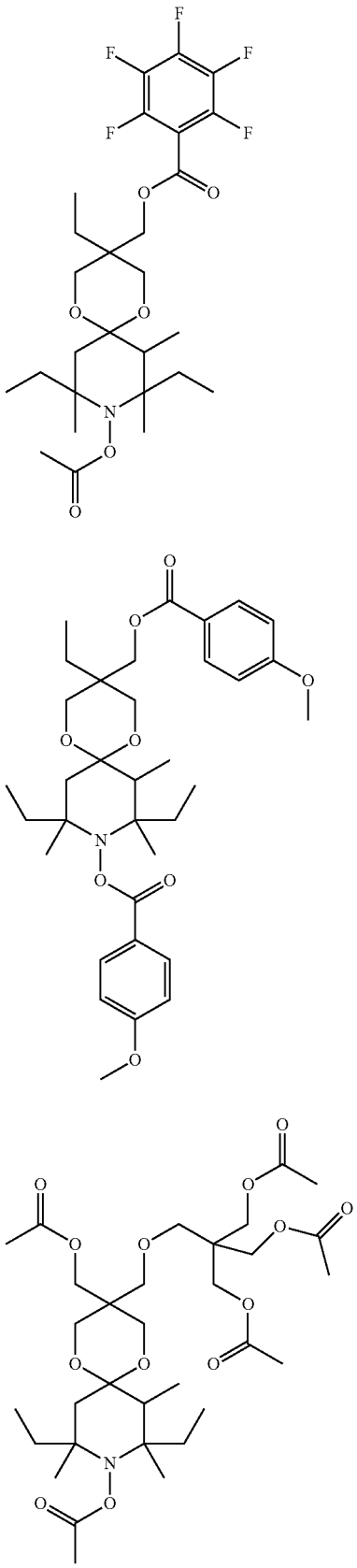

29
-continued
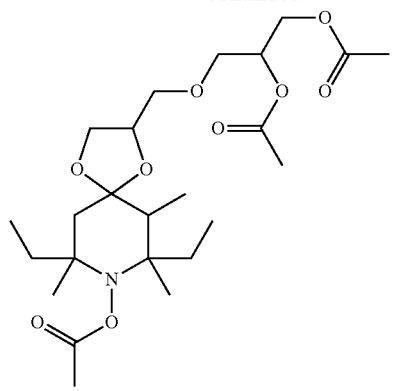
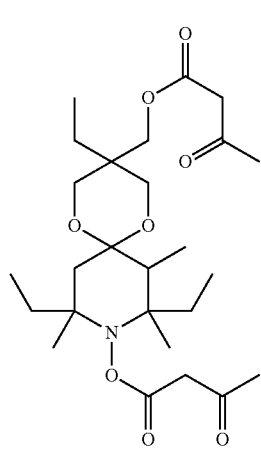
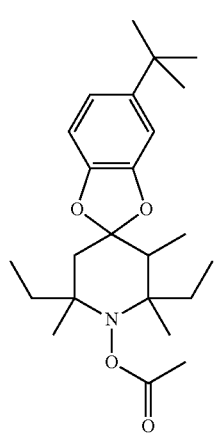
30
-continued
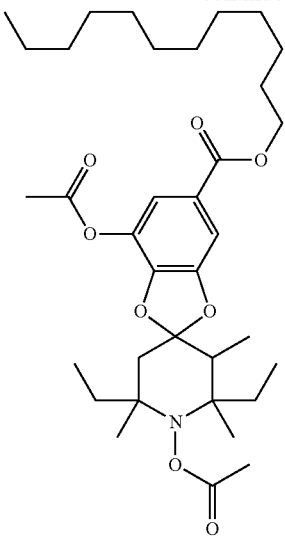
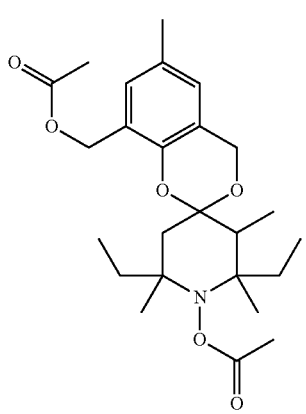
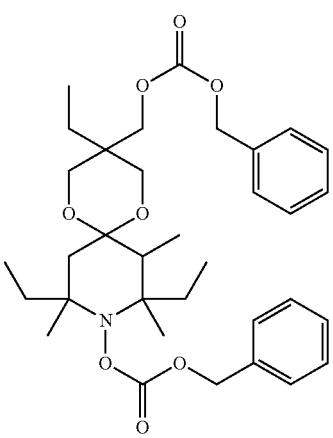

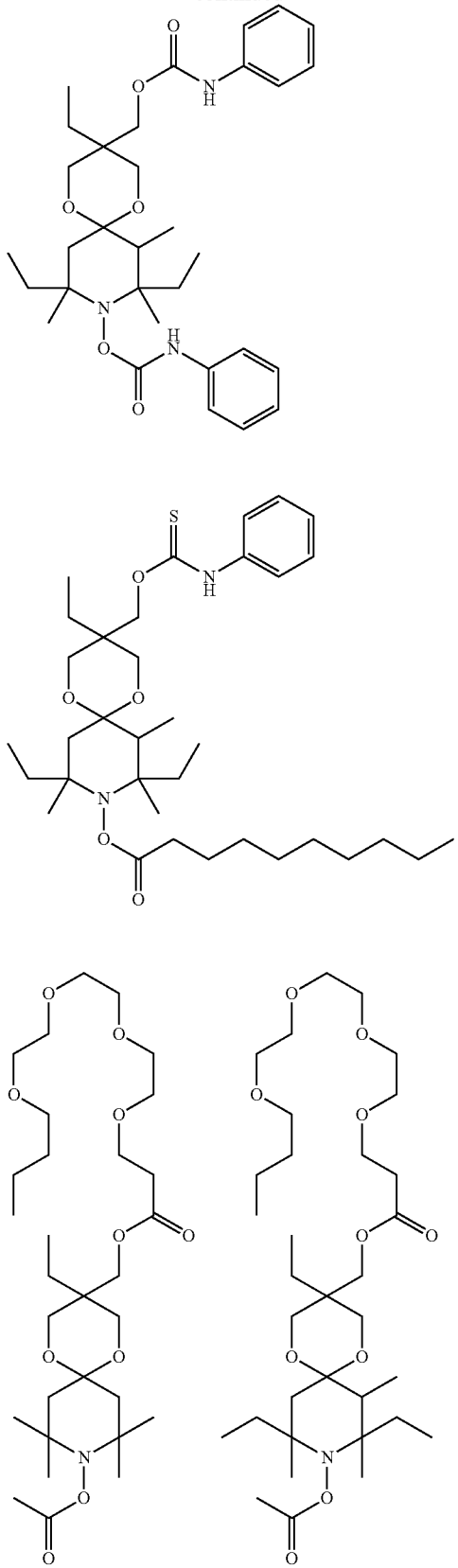

The invention further relates to novel compounds of the formula IA'

R₁-R₄ each represent $C_1$-$C_6$alkyl; and
R₅ and R₆ each represent independently of one another hydrogen, $C_1$-$C_6$alkyl or $C_6$-$C_{10}$aryl; or R₅ and R₆ together represent oxygen, Ra is an acyl radical selected from —C(=O)—H, —C(=O)—$C_1$-$C_{32}$alkyl, —C(=O)—$C_2$-$C_{32}$alkenyl, —C(=O)—$C_2$-$C_4$alkylene-$C_6$-$C_{10}$aryl, C(=O)—$C_2$-$C_4$alkylene-C(=O)—$C_1$-$C_{32}$alkyl, —C(=O)—$C_6$-$C_{10}$aryl, —C(=O)—O—$C_1$-$C_{32}$alkyl, —C(=O)—O-benzyl, —C(=O)—O—$C_6$-$C_{10}$aryl, —C(=O)—NH—$C_1$-$C_{32}$alkyl, —C(=O)—NH—$C_6$-$C_{10}$aryl and —C(=O)—N($C_1$-$C_{32}$alkyl)₂, wherein $C_1$-$C_{32}$alkyl and $C_6$-$C_{10}$aryl may be optionally interrupted by one or more O or C=O and/or substituted by one or more halogen, OR₉, COOR₉, CONR₉R₁₀, phenyl or phenyl substituted by halogen, $C_1$-$C_{32}$alkyl, $C_1$-$C_4$haloalkyl, SR₉, OR₉, or NR₉R₁₀; wherein R₉ and R₁₀ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O;

G $C_1$-$C_{32}$alkyl or —C(=O)—$C_1$-$C_{32}$alkyl, wherein $C_1$-$C_{32}$alkyl is interrupted by one or more C=O and/or substituted by one or more halogen, OR₉, COOR₉, CONR₉R₁₀, phenyl or phenyl substituted by halogen, $C_1$-$C_{32}$alkyl, $C_1$-$C_4$haloalkyl, SR₉, OR₉, or NR₉R₁₀; or G is —C(=O)—$C_4$-$C_{20}$cycloalkyl, —C(=O)—$C_2$-$C_{32}$alkenyl, —C(=O)—$C_2$-$C_4$alkylene-$C_6$-$C_{10}$aryl, C(=O)—$C_2$-$C_4$alkylene-C(=O)$C_1$-$C_{32}$alkyl, or —C(=O)—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, OR₉, CONR₉R₁₀, phenyl or phenyl substituted by halogen, $C_1$-$C_{32}$alkyl, $C_1$-$C_4$haloalkyl, SR₉, OR₉, or NR₉R₁₀ and/or $C_1$-$C_{32}$alkyl and $C_4$-$C_{20}$cycloalkyl may be interrupted by one or more O or C=O; or $C_4$-$C_{20}$cycloalkyl, —C(=O)—O—$C_1$-$C_{32}$alkyl, —C(=O)—O—$C_6$-$C_{10}$aryl, —C(=O)—NH—$C_1$-$C_{32}$alkyl, —C(=O)—NH—$C_6$-$C_{10}$aryl —C(=O)—N($C_1$-$C_{32}$alkyl)₂ or —C(=S)—NH—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, OR₉, COOR₉, CONR₉R₁₀, phenyl or phenyl substituted by halogen, $C_1$-$C_{32}$alkyl, $C_1$-$C_4$haloalkyl, SR₉, OR₉, or NR₉R₁₀ and/or $C_1$-$C_{32}$alkyl and $C_4$-$C_{20}$cycloalkyl may be interrupted by one or more O or C=O;

R₉ and R₁₀ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O.

Ra is formula IA' is preferably an acyl radical selected from —C(=O)—$C_1$-$C_{32}$alkyl, —C(=O)—$C_2$-$C_4$alkylene-C(=O)—$C_1$-$C_{32}$alkyl, —C(=O)-phenyl or —C(=O)-phenyl substituted by methoxy, —C(=O)—O—$C_1$-$C_{32}$alkyl, —C(=O)—O-benzyl, —C(=O)—NH—$C_1$-$C_{32}$alkyl, —C(=O)—NH-phenyl.

G is preferably —C(=O)—C$_1$-C$_{32}$alkyl, —C(=O)—C$_2$-C$_4$alkylene-C(=O)C$_1$-C$_{32}$alkyl; or G is —C(=O)—C$_2$-C$_4$alkenyl-phenyl, or —C(=O)-phenyl, wherein phenyl may be optionally substituted by one or more halogen, OR$_9$.

Examples of novel compounds of the formula A' are

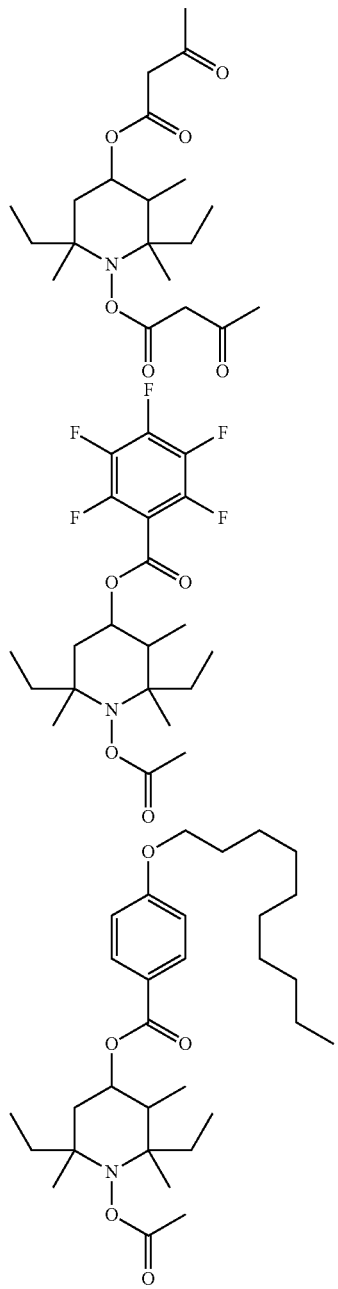

Preparation of the Novel Compounds

General Process to Prepare the Novel Compounds

The above-described novel compounds can be prepared in a manner known per se. The preparation of these compounds is likewise the subject-matter of the invention and can be carried out in the customary reactions, for example, by N-oxidation of an appropriate piperidine and reduction of the resulting nitroxyl radical to hydroxylamine, followed by esterification of the hydroxylamine with an acid R$_a$—H which introduces the group R$_a$ and corresponds to an acyl radical selected, for example, from the group consisting of —C(=O)—H, —C(=O)—C$_1$-C$_{32}$alkyl, —C(=O)—C$_2$-C$_{32}$alkenyl, —C(=O)—C$_2$-C$_4$alkenyl-C$_6$-C$_{10}$aryl, —C(=O)—C$_6$-C$_{10}$aryl, —C(=O)—O—C$_1$-C$_{32}$alkyl, —C(=O)—O—C$_6$-C$_{10}$aryl, —C(=O)—NH—C$_1$-C$_{32}$alkyl, —C(=O)—NH—C$_6$-C$_{10}$aryl and —C(=O)—N(C$_1$-C$_{32}$alkyl)$_2$, wherein C$_1$-C$_{32}$alkyl and C$_6$-C$_{10}$aryl may be optionally interrupted by one or more O or C=O and/or substituted by one or more halogen, OR$_9$, COOR$_9$, CONR$_9$R$_{10}$, phenyl or phenyl substituted by halogen, C$_1$-C$_{32}$alkyl, C$_1$-C$_4$haloalkyl, SR$_9$, OR$_9$, or NR$_9$R$_{10}$ or a reactive functional derivative thereof, e.g. the acid halide R$_a$—X, e.g. the acid chloride, or anhydride, e.g. (R$_a$)$_2$O.

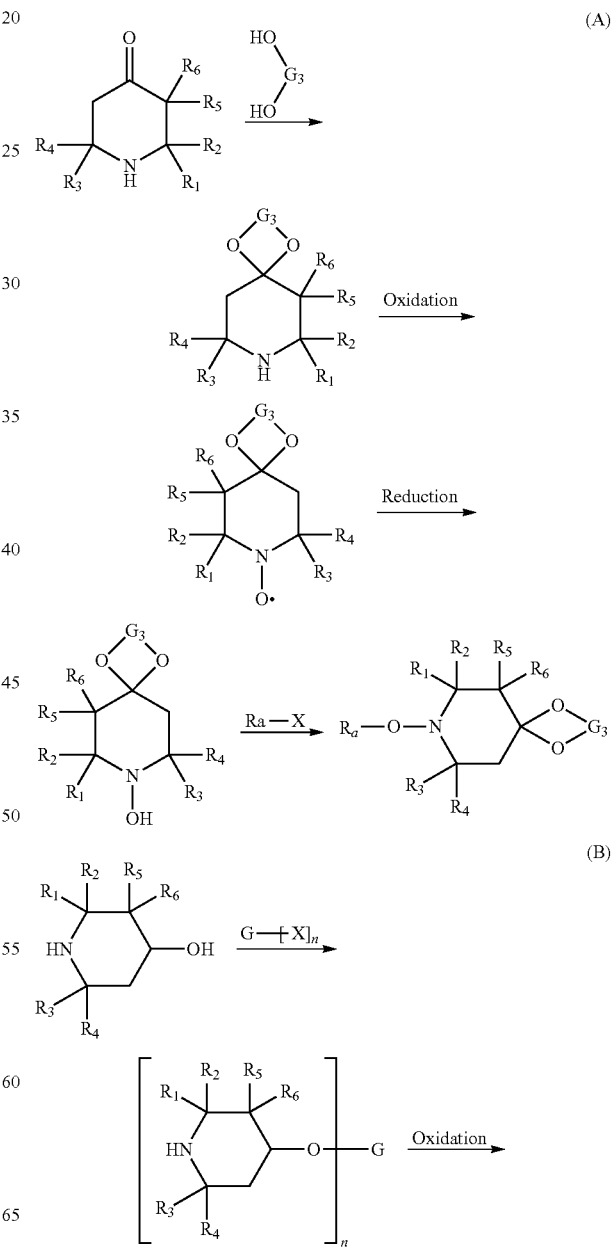

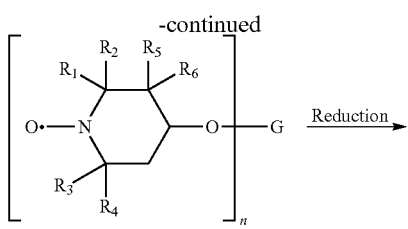
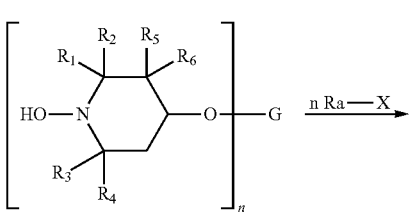
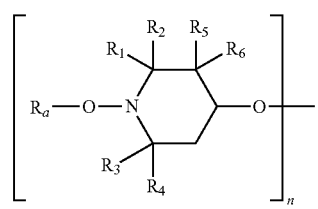
Another synthesis scheme is as follows:
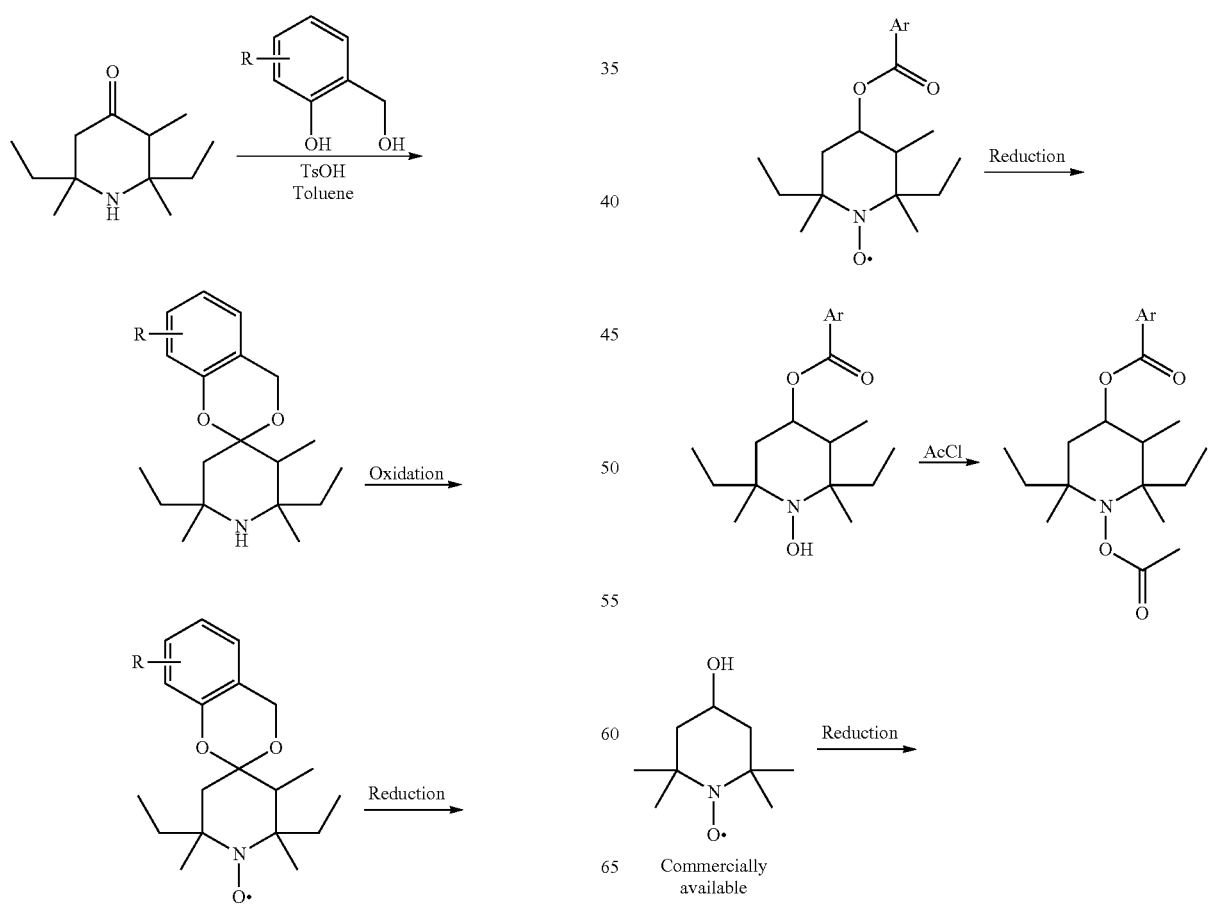
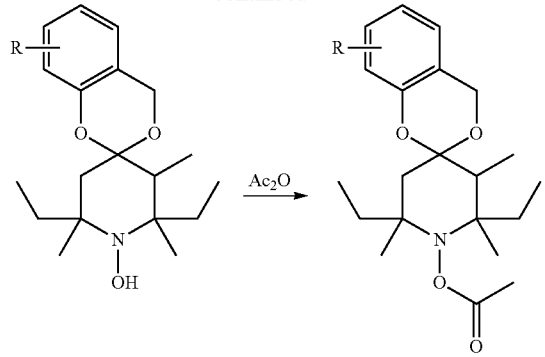

-continued

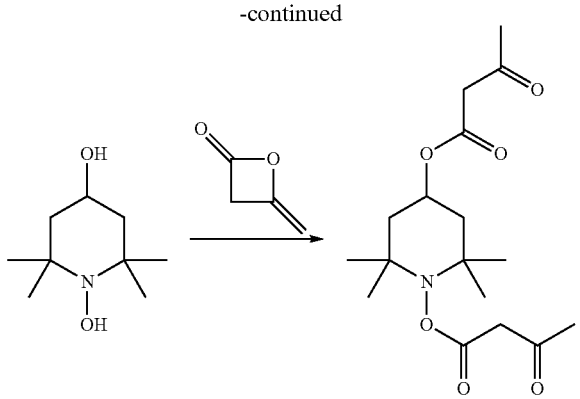

The novel compounds are in one embodiment prepared by starting from e.g. from

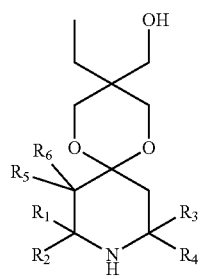

a) adding the acid Ra"—CH$_2$—CH$_2$—COOH to a compound
b) oxidizing
c) acylation
wherein Ra" and R1-R6 are as defined above.

Ketalation of piperidinone with the corresponding cathecol or o-hydroxymethylphenol can give the new core structures as shown above.

Compositions

The novel compounds can be used as thermal initiators not only to polymerize color resist binders but to polymerize ethylenically unsaturated monomers in general.

Thus, the invention relates to a radically polymerizable composition comprising:
(a) at least one alkaline developable resin;
(b) at least one acrylate monomer;
(c) at least a photoinitiator; and
(d) at least one hydroxylamine ester compound of formula IA' and IC'.

Thus the invention further relates to a composition comprising
at least one ethylenically unsaturated, polymerizable monomer or oligomer; and
at least one of the above-described compounds (IA') and (IC').

Thus the invention further relates to a process for preparing an oligomer, a cooligomer, a polymer or a copolymer by free-radical polymerization, characterised in that a composition comprising
α) at least one ethylenically unsaturated, polymerizable monomer or oligomer; and
α) one of the above-defined novel compounds (IA') and (IC') is subjected to the reaction conditions of a free-radical polymerization.

Suitable ethylenically unsaturated monomers or oligomers can be polymerized in a manner known per se using the methods of free-radical polymerization.

Monomers suitable for free-radical polymerization are, for example, ethylenically unsaturated polymerizable monomers selected from the group consisting of alkenes, conjugated dienes, styrenes, acrolein, vinyl acetate, vinylpyrrolidone, vinylimidazole, maleic anhydride, acrylic acid, acrylic acid derivatives, vinyl halides and vinylidene halides.

Examples of alkenes and conjugated alkenes are ethylene, isoprene, 1,3-butadiene and a-C5-Cisalkenes.

Suitable styrenes may be substituted on the phenyl group by from one to three substituents selected from the group consisting of hydroxy, C1-C4alkoxy, e.g. methoxy or ethoxy, halogen, e.g. chlorine, amino and C1-C4alkyl, e.g. methyl or ethyl.

Suitable acrylic acid derivatives are selected, for example, from the group consisting of C1-C4alkylacrylic acids, amides, nitriles, anhydrides and salts of acrylic acid and of C1 C4alkylacrylic acids, C1-C24alkyl acrylates and C1-C24alkyl C1-C4alkylacrylates.

Particularly preferred acrylic acid derivatives are methacrylic acid or salts thereof, acrylic anhydride and methacrylic anhydride, C1-C24alkyl acrylates and methacrylates, mono- or di-C1-C4alkylamino-C2-C4alkyl acrylates and methacrylates, hydroxy-C2-C4alkyl acrylates and methacrylates, (C1-C4alkyl)$_3$silyloxy-C2-C4alkyl acrylates and methacrylates, (C1-C4alkyl) 3silyl-C2-C4alkyl acrylates and methacrylates, heterocyclyl-C2-C4alkyl acrylates and methacrylates, acrylic and methacrylic esters having poly-C2-C4alkylene glycol ester groups which may in turn be esterified by substituted C1-C24alkoxy groups, acrylamides and methacrylamides, mono- or di-C1-C4alkylamides of acrylic and methacrylic acids, amino-C2-C4alkylamides of acrylic and methacrylic acids and acrylonitrile.

Suitable salts of acrylic acid or methacrylic acid are, for example, (C1-C4alkyl)$_4$ammonium or (C1-C4alkyl)$_3$NH salts, e.g. the tetramethylammonium, tetraethylammonium, trimethylammo-nium or triethylammonium salt, the trimethyl-2-hydroxyethylammonium or triethyl-2-hydroxyethylammonium salt, the dimethyl-2-hydroxyethylammonium or diethyl-2-hydroxyethylam-monium salt.

Suitable C1-C24alkyl acrylates and methacrylates are esterified by, for example, methyl, ethyl, n-butyl, isobutyl, tert-butyl, 2-ethylhexyl, isobornyl, isodecyl, lauryl, myristyl, stearyl or behenyl.

Examples of mono- or di-C1-C4alkylamino-C2-C4alkyl acrylates and methacrylates are 2monomethylaminoethyl acrylate or methacrylate, 2-dimethylaminoethyl acrylate or methacrylate and the corresponding 2-monoethylaminoethyl or 2-diethylaminoethyl esters and also 2-tert-butylaminoethyl acrylate or methacrylate.

Examples of hydroxy-C2-C4alkyl acrylates and methacrylates are 2-hydroxyethyl acrylate or methacrylate (HEA, HEMA) and 2-hydroxypropyl acrylate or methacrylate (HPA, HPMA).

Examples of silyloxy-C2-C4alkyl acrylates and methacrylates are 2-trimethylsilyloxyethyl acrylate or methacrylate (TMS-HEA, TMS-HEMA). Examples of (C1-C4alkyl) 3silyl-C2-C4alkyl acrylates and methacrylates are 2-trimethylsilylethyl acrylate or methacrylate and 3-trimethylsilyl-n-propyl acrylate or methacrylate.

Acrylic or methacrylic esters having poly-C2-C4alkylene glycol ester groups which may in turn be esterified by substituted C1-C24alkoxy groups have the formula: EMI12.1 where R1 and R2 are each, independently of one another, hydrogen or methyl and R3 is C1-C24alkyl, e.g. methyl, ethyl, n-propyl or isopropyl, n-butyl, isobutyl or tert-butyl, n-pentyl or neopentyl, lauryl, myristyl or stearyl, or aryl-C1,-

C24alkyl, e.g. benzyl or phenyl-n-nonyl, or else C1-C24alkylaryl or C1-C24alkylaryl-C1-C24alkyl.

Examples of heterocycyl-C2-C4alkyl acrylates and methacrylates are 2-(N-morpholinyl,-2 pyridyl,-1-imidazolyl,-2-oxo-1-pyrrolidinyl,-4-methylpiperidin-1-yl or -2-oxoimidazolidin-1-yl)ethyl acrylate or methacrylate.

Examples of the abovementioned mono- or di-C1-C4alkyl amides of acrylic acid and meth acrylic acid, di-C1-C4alkylamino-C2-C4alkylamides of acrylic acid and methacrylic acid or amino-C2-C4alkylamides of acrylic acid and methacrylic acid are N,N-dimethylacrylamide, N,N-dimethyl (meth)acrylamide, 2-(N,N-dimethylaminoethyl)acrylamide, 2-(N,N-dimethylami-noethyl)methacrylamide, 2-aminoethylacrylamide and 2-aminoethylmethacrylamide.

The abovementioned acrylic acid derivatives are present in the polymerizable composition as monomers or in admixture with acrylic acid.

In the composition, the component B) is present in a ratio to the component A) of from 0.01 to 30 mol %, preferably from 0.05 to 10 mol %, particularly preferably from 0.1 to 1.0 mol %.

The new compounds can also be used in a mixture of known hydroxylaminesters.

The novel compounds of the formula IA' and IC' can also be used for reducing the molecular weight of polypropylene, propylene copolymers or polypropylene blends. These kind of process is described in WO2006027327.

Colorants:

Pigments may be present. The pigments which can be comprised in the composition according to the present invention, including a pigmented color filter resist composition, are preferably processed pigments.

The red pigment comprises, for example, an anthraquinone type pigment alone, a diketopyrolopyrole type pigment alone, a mixture of them or a mixture consisting of at least one of them and a disazo type yellow pigment or an isoindoline type yellow pigment, in particular C. I. Pigment Red 177 alone, C. I. Pigment Red 254 alone, a mixture of C. I. Pigment Red 177 and C. I. Pigment Red 254 or a mixture consisting of at least one member of C. I. Pigment Red 177, C. I. Pigment Red 242 and C. I. Pigment Red 254, and C. I. Pigment Yellow 83 or C. I. Pigment Yellow 139 ("C.I." refers to the Color Index, known to the person skilled in the art and publicly available).

Further suitable examples for the pigment are C.I. Pigment Red 9, 97, 105, 122, 123, 144, 149, 168, 176, 179, 180, 185, 202, 207, 209, 214, 222, 244, 255, 264, 272 and C.I. Pigment Yellow 12, 13, 14, 17, 20, 24, 31, 53, 55, 93, 95, 109, 110, 128, 129, 138, 139, 150, 153, 154, 155, 166, 168, 185, 199, 213 and C.I. Pigment Orange 43 and 71.

Examples of the dyes for red color are C. I. Solvent Red 25, 27, 30, 35, 49, 83, 89, 100, 122, 138, 149, 150, 160, 179, 218, 230, C. I. Direct Red 20, 37, 39, 44, and C. I. Acid Red 6, 8, 9, 13, 14, 18, 26, 27, 51, 52, 87, 88, 89, 92, 94, 97, 111, 114, 115, 134, 145, 151, 154, 180, 183, 184, 186, 198, C. I. Basic Red 12, 13, C. I. Disperse Red 5, 7, 13, 17 and 58. The Red dyes can be used in combination with yellow and/or orange dyes.

The green pigment comprises for instance a halogenated phthalocyanine type pigment alone or its mixture with a disazo type yellow pigment, an quinophthalone type yellow pigment or a metal complex, in particular C. I. Pigment Green 7 alone, C. I. Pigment Green 36 alone, or a mixture consisting of at least one member of C. I. Pigment Green 7, C. I. Pigment Green 36 and C. I. Pigment Yellow 83, C. I. Pigment Yellow 138 or C. I. Pigment Yellow 150. Other suitable green pigments are C.I. Pigment Green 15, 25 and 37.

Examples for suitable green dyes are C. I. Acid Green 3, 9, 16, C. I. Basic Green 1 and 4.

Examples for suitable blue pigments are phthalocyanine type pigments, used either alone or in combination with an dioxazine type violet pigment, for instance, C. I. Pigment Blue 15:6 alone, a combination of C. I. Pigment Blue 15:6 and C. I. Pigment Violet 23. Further examples for blue pigments are such of C. I. Pigment Blue 15:3, 15:4, 16, 22, 28 and 60. Other suitable pigments are C. I. Pigment Violet 14, 19, 23, 29, 32, 37, 177 and C. I. Orange 73.

Examples for suitable blue dyes are C. I. Solvent Blue 25, 49, 68, 78, 94, C. I. Direct Blue 25, 86, 90, 108, C. I. Acid Blue 1, 7, 9, 15, 103, 104, 158, 161, C. I. Basic Blue 1, 3, 9, 25, and C. I. Disperse Blue 198.

The pigment of the photopolymeric composition for black matrix preferably comprises at least one member selected from the group consisting of carbon black, titanium black and iron oxide. Preferred example is carbon black. However, a mixture of other pigments which, in total, give the black appearance, can also be used. For example, also C. I. Pigment Black 1, 7 and 31 can be used alone or in combination.

Other examples of the dyes used for color filter are C. I. Solvent Yellow 2, 5, 14, 15, 16, 19, 21, 33, 56, 62, 77, 83, 93, 162, 104, 105, 114, 129, 130, 162, C. I. Disperse Yellow 3, 4, 7, 31, 54, 61, 201, C. I. Direct Yellow 1, 11, 12, 28, C. I. Acid Yellow 1, 3, 11, 17, 23, 38, 40, 42, 76, 98, C. I. Basic Yellow 1, C. I. Solvent Violet 13, 33, 45, 46, C. I. Disperse Violet 22, 24, 26, 28, C. I. Acid Violet 49, C. I. Basic Violet 2, 7, 10, C. I. Solvent Orange 1, 2, 5, 6, 37, 45, 62, 99, C. I. Acid Orange 1, 7, 8, 10, 20, 24, 28, 33, 56, 74, C. I. Direct Orange 1, C. I. Disperse Orange 5, C. I. Direct Brown 6, 58, 95, 101, 173, C. I. Acid Brown 14, C. I. Solvent Black 3, 5, 7, 27, 28, 29, 35, 45 and 46.

In some special cases of manufacturing color filters, complementary colors, yellow, magenta, cyan and optionally green, are used instead of red, green and blue. As yellow for this type of color filters, the abovementioned yellow pigments and dyes can be employed. Examples of the colorants suitable for magenta color are C. I. Pigment Red 122, 144, 146, 169, 177, C. I. Pigment Violet 19 and 23. Examples of cyan color are aluminum phthalocyanine pigments, titanium phthalocyanine pigments, cobalt phthalocyanine pigments, and tin phthalocyanine pigments.

The pigments in the color filter resist composition have preferably a mean particle diameter smaller than the wavelength of visible light (400 nm to 700 nm). Particularly preferred is a mean pigment diameter of <100 nm.

The concentration of the pigment in the total solid component (pigments of various colors and resin) is for example in the range of 5% to 80% by weight, in particular in the range of 20% to 65% by weight.

If necessary, the pigments may be stabilized in the photosensitive composition by pretreatment of the pigments with a dispersant to improve the dispersion stability of the pigment in the liquid formulation. Suitable additives are described below.

Additives

Additives are optional present such as dispersing agents, surfactant, adhesion promoters, photosensitizer and the like.

It is preferred to apply a surface treatment to the pigments in order to make the pigment easy to disperse and to stabilize the resultant pigment dispersion. The surface treatment reagents are, for example, surfactants, polymeric dispersants, general texture improving agents, pigment derivatives and mixtures thereof. It is especially preferred when the colorant composition according to the invention comprises at least one polymeric dispersant and/or at least pigment derivative.

Suitable surfactants include anionic surfactants such as alkylbenzene- or alkylnahthalene-sulfonates, alkylsulfosuccinates or naphthalene formaldehyde sulfonates; cationic surfactants including, for example, quaternary salts such as benzyl tributyl ammonium chloride; or nonionic or amphoteric surfactants such as polyoxyethylene surfactants and alkyl- or amidopropyl betaines, respectively.

Illustrative examples of the surfactant include polyoxyethylene alkyl ethers such as polyoxyethylene lauryl ether, polyoxyethylene stearyl ether and polyoxyethylene oleyl ether; polyoxyethylene alkylphenyl ethers such as polyoxyethylene octylphenyl ether and polyoxyethylene nonylphenyl ether; polyethylene glycol diesters such as polyethylene glycol dilaurate and polyethylene glycol distearate; sorbitan fatty acid esters; fatty acid modified polyesters; tertiary amine modified polyurethanes; polyethyleneimines; those available under the trade names of KP (a product of Shin-Etsu Chemical Co., Ltd), Polyflow (a product of KYOEISHA CHEMICAL Co., Ltd), F-Top (a product of Tochem Products Co., Ltd), MEGAFAC (a product of Dainippon Ink & Chemicals, Inc.), Fluorad (a product of Sumitomo 3M Ltd), Asahi Guard and Surflon (products of Asahi Glass Co., Ltd); and the like.

These surfactants may be used alone or in admixture of two or more.

The surfactant is generally used in an amount of 50 parts or less by weight, preferably 0 to parts by weight, based on 100 parts by weight of the colorant composition.

Polymeric dispersants include high molecular weight polymers with pigment affinic groups. Examples are: statistical co-polymers comprised from, for instance, styrene derivatives, (meth)acrylates and (meth)acrylamides, and such statistical co-polymers modified by post modification; block co-polymers and/or comb polymers comprised from, for instance, styrene derivatives, (meth)acrylates and (meth)acrylamides, and such block co-polymers and/or comb polymers modified by post modification; polyethylenimines, which for instance is crafted with polyesters; polyamines, which for instance is crafted with polyesters; and many kinds of (modified) polyurethanes.

Polymeric dispersants may also be employed. Suitable polymeric dispersants are, for example, BYK's DISPERBYK® 101, 115, 130, 140, 160, 161, 162, 163, 164, 166, 168, 169, 170, 171, 180, 182, 2000, 2001, 2009, 2020, 2025, 2050, 2090, 2091, 2095, 2096, 2150, Ciba's Ciba® EFKA® 4008, 4009, 4010, 4015, 4046, 4047, 4050, 4055, 4060, 4080, 4300, 4310, 4330, 4340, 4400, 4401, 4402, 4403, 4406, 4500, 4510, 4520, 4530, 4540, 4550, 4560, Ajinomoto Fine Techno's PB®711, 821, 822, 823, 824, 827, Lubrizol's SOLSPERSE® 1320, 13940, 17000, 20000, 21000, 24000, 26000, 27000, 28000, 31845, 32500, 32550, 32600, 33500, 34750, 36000, 36600, 37500, 39000, 41090, 44000, 53095 and combinations thereof.

It is preferred to use Ciba® EFKA® 4046, 4047, 4060, 4300, 4310, 4330, 4340, DISPERBYK® 161, 162, 163, 164, 165, 166, 168, 169, 170, 2000, 2001, 2020, 2050, 2090, 2091, 2095, 2096, 2105, 2150, PB®711, 821, 822, 823, 824, 827, SOLSPERSE® 24000, 31845, 32500, 32550, 32600, 33500, 34750, 36000, 36600, 37500, 39000, 41090, 44000, 53095 and combinations thereof as dispersant.

Suitable texture improving agents are, for example, fatty acids such as stearic acid or behenic acid, and fatty amines such as laurylamine and stearylamine. In addition, fatty alcohles or ethoxylated fatty alcohles polyols such as aliphatic 1,2-diols or epoxidized soy bean oil, waxes, resin acids and resin acid salts may be used for this purpose.

Suitable pigment derivatives are, for example, copper phthalocyanine derivatives such as Ciba's Ciba® EFKA® 6745, Lubrizol's SOLSPERSE® 5000, 12000, BYK's SYNERGIST 2100 and azo derivatives such as Ciba® EFKA® 6750, SOLSPERSE® 22000 and SYNERGIST 2105.

The above mentioned dispersants and surfactants for pigments are for example employed in compositions of the present invention which are used as resist formulations, in particular in color filter formulations.

Subject of the invention also is a photopolymerizable composition as described above as further additive comprising a dispersant or a mixture of dispersants as well as a photopolymerizable composition as described above as further additive comprising a pigment or a mixture of pigments.

In the invention, the content of the dispersing agent is preferably from 1 to 80% by mass, more preferably from 5 to 70% by mass, even more preferably from 10 to 60% by mass, based on the mass of the pigment.

Adhesion Improving Agent

The curable composition of the invention may contain an adhesion improving agent for increasing adhesion to a hard surface, such as of a support. The adhesion improving agent may be a silane coupling agent, a titanium coupling agent or the like.

Photosensitizer

Photopolymerization can also be accelerated by adding further photosensitizers or coinitiators which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes. Specific examples of such compounds are 1. Thioxanthones Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]-thioxanthone, 1,3-dimethyl-2-hydroxy-9Hthioxanthen-9-one 2-ethylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone, 4,4'-bis(dimethylamino)-benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoyl-phenylsulfanyl)-phenyl]-2-methyl-2-(toluene-4-sulfonyl)-propan-1-one, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl 1,4,7,10,13-pentaoxamidecyl)-benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroyl-coumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-di-methylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino) ethyl benzoate, poly(propylenegylcol)-4-(dimethylamino) benzoate.

A photosensitizer may be selected from the group consisting of benzophenone and its derivatives, thioxanthone and its derivatives, anthraquinone and its derivatives, or coumarin and its derivatives.

Accelerater

To accelerate the photopolymerization it is possible to add amines, for example triethanolamine, N-methyldiethanolamine, ethyl-p-dimethylaminobenzoate, 2-(dimethylamino) ethyl benzoate, 2-ethylhexyl-p-dimethylaminobenzoate, octyl-para-N,N-dimethylaminobenzoate, N-(2-hydroxyethyl)-N-methyl-para-toluidine or Michler's ketone. The action of the amines can be intensified by the addition of aromatic ketones of the benzophenone type. Examples of amines which can be used as oxygen scavengers are substituted N,N-dialkylanilines, as are described in EP339841. Other accelerators, coinitiators and autoxidizers are thiols, thioethers, disulfides, phosphonium salts, phosphine oxides or phosphines, as described, for example, in EP438123, in GB2180358 and in JP Kokai Hei 6-68309.

The choice of additive(s) is made depending on the field of application and on properties required for this field. The additives described above are customary in the art and accordingly are added in amounts which are usual in the respective application.

Solvents:

Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, ethylene glycol monomethyl ether, ethylene glycol monoethyl ether, ethylene glycol monopropyl ether, ethylene glycol monobutyl ether, ethylene glycol dimethyl ether, ethylene glycol diethyl ether, ethylene glycol dipropyl ether, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol dipropyl ether, diethylene glycol monomethyl ether, diethylene glycol monoethyl ether, diethylene glycol dimethyl ether, diethylene glycol diethyl ether, ethylene glycol monomethyl ether acetate, ethylene glycol monoethyl ether acetate, ethylene glycol monopropyl ether acetate, ethylene glycol monobutyl ether acetate, propylene glycol monomethyl ether acetate, propylene glycol monoethyl ether acetate, propylene glycol monopropyl ether acetate, 2-methoxybutyl acetate, 3-methoxybutyl acetate, 4-methoxybutyl acetate, 2-methyl-3-methoxybutyl acetate, 3-methyl-3-methoxybutyl acetate, 3-ethyl-3-methoxybutyl acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, ethyl acetate, n-butyl acetate, ethyl propionate, propyl propionate, butyl propionate, ethyl 3-ethoxypropionate, methyl 3-methoxypropionate, 2-heptanone, 2-pentanone, and ethyl lactate.

Hybrid System:

The compositions according to this invention can comprise additionally a crosslinking agent which is activated by an acid or a base, for example as described in JP 10 221843-A, and a compound which generates acid or base thermally or by actinic radiation and which activates a crosslinking reaction. Use is made, in addition to the free-radical hardeners, of cationic photo or thermal initiators such as sulfonium-, phosphonium- or iodonium salts, for example IRGACURE® 250, San-Aid SI series, SI-60L, SI-80L, SI-100L, SI-110L, SI-145, SI-150, SI-160, SI-180L provided by Sanshin Chemical, cyclopentadienyl-arene-iron(II) complex salts, for example ($\eta^6$-iso-propylbenzene)($\eta^5$-cyclopentadienyl)iron (II) hexafluorophosphate, as well as oxime sulfonic acid esters, for example described in EP 780729. Also pyridinium and (iso)quinolinium salts as described e.g. in EP 497531 and EP 441232 may be used in combination with the new photo-initiators. Examples of bases are imidazole and its derivatives for example Curezole OR series and CN series provided by Shikoku Chemicals.

The crosslinking agents which can be activated by acid or base include compounds having epoxy or oxetane groups. There may be used a solid or liquid known epoxy or oxetane compound and said compound is used depending on required characteristics. A preferred epoxy resin is a bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; a bisphenol A type epoxy resin such as Epiculon N-3050, N-7050, N-9050 produced by Dainippon Ink & Chemicals Inc., XAC-5005, GT-7004, 6484T, 6099; a bisphenol F type epoxy resin such as YDF-2004, YDF2007 produced by Tohto Kasei Co., etc.; a bisphenol fluorene type epoxy resin such as OGSOL PG, PG-100, EG, EG-210 produced by Osaka Gas Chemicals; a diglycidyl phthalate resin such as Blemmer DGT produced by Nippon Oil and Fats Co., Ltd., etc.; a heterocyclic epoxy resin such as TEPIC produced by Nissan Chemical Industries, Ltd., Araldite PT810 produced by Ciba Specialty Chemicals Inc., etc.; a bixylenol type epoxy resin such as YX-4000 produced by Yuka Shell Co., etc.; a biphenol type epoxy resin such as YL-6056 produced by Yuka Shell Co., etc.; a tetraglycidyl xylenoylethane resin such as ZX-1063 produced by Tohto Kasei Co., etc.; a novolak type epoxy resin such as EPPN-201, EOCN-103, EOCN-1020, EOCN-1025 and BRRN produced by Nippon Kayaku Co., Ltd., ECN-278, ECN-292 and ECN-299 produced by Asahi Chemical Industry Co., Ltd., GY-1180, ECN-1273 and ECN-1299 produced by Ciba Specialty Chemicals Inc., YDCN-220L, YDCN-220HH, YDCN-702, YDCN-704, YDPN-601 and YDPN-602 produced by Tohto Kasei Co., Epiculon-673, N-680, N-695, N-770 and N-775 produced by Dainippon Ink & Chemicals Inc., etc.; a novolak type epoxy resin of bisphenol A such as EPX-8001, EPX-8002, EPPX-8060 and EPPX-8061 produced by Asahi Chemical Industry Co., Ltd., Epiculon N-880 produced by Dainippon Ink & Chemicals Inc., etc.; a chelate type epoxy resin such as EPX-49-69 and EPX-49-30 produced by Asahi Denka Kogyo K.K., etc.; a glyoxal type epoxy resin such as YDG-414 produced by Tohto Kasei Co., etc.; an amino group-containing epoxy resin such as YH-1402 and ST-110 produced by Tohto Kasei Co., YL-931 and YL-933 produced by Yuka Shell Co., etc.; a rubber-modified epoxy resin such as Epiculon TSR-601 produced by Dainippon Ink & Chemicals Inc., EPX-84-2 and EPX-4061 produced by Asahi Denka Kogyo K.K., etc.; a dicyclopentadiene phenolic type epoxy resin such as DCE-400 produced by Sanyo-Kokusaku Pulp Co., Ltd., etc.; a silicone-modified epoxy resin such as X-1359 produced by Asahi Denka Kogyo K.K., etc.; an -caprolactone-modified epoxy resin such as Plaque G-402 and G-710 produced by Dicel Chemical Industries, Ltd., etc. and others. Further, partially esterified compounds of these epoxy compounds (e.g. esterified by (meth)acrylates) can be used in combination. Examples of oxetan compounds are 3-ethyl-3-hydroxymethyloxetane (oxetane alcohol), 2-ethylhexyloxetane, xylene bisoxetane, 3-ethyl-3-[[(3-ethyloxetane-3-yl)methoxy]methyl]oxetane (Aron Oxetane series) provided by Toagosei.

The invention further relates to the use of the photoresist composition to manufacture color filters for a variety of display applications and for image sensors such as charge coupled device (CCD) and complementary metal-oxide semiconductor (CMOS), spacers for LCD, overcoat layer for color filter and LCD, sealant for LCD, optical films for a variety of display applications, insulation layer for LCD, resists or photosensitive compositions to generate structures or layers in the manufacturing processes of plasma-display panels, electroluminescence displays and LCD, solder resists, as a photoresist material used for forming dielectric layers in a sequential build-up layer of a printed circuit board.

The compositions according to the invention are particularly suitable for the production of color filters or color mosaic systems, such as described, for example, in EP 320 264. The color filters can be used, for example, for flat panel display technology such as LCD, electroluminescent display and plasma display, for image sensors such as CCD and CMOS, and the like.

The color filters usually are prepared by forming red, green and blue pixels and black matrix on a glass substrate. In these processes photocurable compositions according to the invention can be employed. A particularly preferred method of use comprises adding of the coloring matters, dyes and pigments of red, green and blue colors to the light-sensitive resin composition of the present invention, coating of the substrate with the composition, drying of the coating with a short heat treatment, patternwise exposure of the coating (i.e. through a suitable mask) to actinic radiation and subsequent development of the pattern in a suitable aqueous alkaline developer solution and a heat treatment. Thus, by subsequently applying a red, green, blue and black pigmented coating, in any desired order, on top of each other with this process a color filter layer with red, green and blue color pixels and black matrix can be produced.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

The developer solution can be used in all forms known to the person skilled in the art, for example in form of a bath solution, puddle, or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 2 to about 60 minutes.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. No. 5,368,976; U.S. Pat. No. 5,800,952; U.S. Pat. No. 5,882, 843; U.S. Pat. No. 5,879,855; U.S. Pat. No. 5,866,298; U.S. Pat. No. 5,863,678; JP 06-230212-A; EP320264; JP 09-269410-A; JP 10-221843-A; JP 01-090516-A; JP 10-171119-A, U.S. Pat. No. 5,821,016, U.S. Pat. No. 5,847, 015, U.S. Pat. No. 5,882,843, U.S. Pat. No. 5,719,008, EP881541, or EP902327.

Instead of forming a black matrix using a photosensitive composition and patterning the black photosensitive composition photolithographically by patternwise exposure to form the black pattern separating the red green and blue coloured areas on the tranparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

Different Uses.

The invention further relates to the use of the of hydroxylamine esters of the formula I to improve the C=C conversion rate in the post baking process.

The invention further relates to the production of color filters.

A method for producing a color filter comprising:
a) applying the photopolymerizable composition to a support;
b) drying the photopolymerizable composition
c) exposing the photopolymerizable composition to UV light through a mask;
d) developing the exposed composition layer with an alkali developer to form a colored pattern.
e) post baking the exposed photoresist at 180 to 230° C.

The novel hydroxylamine-esters can be used as the known ones to prepare coating optionally in combination with known initiators (-photo-radical, photo-acid&base, thermal-acid&base) under different curing conditions (heat, NIR, e-beam).

The novel hydroxylamine-esters can be used as the known ones for the controlled degradation of polypropylene and for the controlled build-up of the molecular weight or crosslinking of polyethylene.

Examples of the support that may be used in this step include silicon wafers, soda glass substrates, PYREX (registered trademark) glass substrates, quartz glass substrates, The curable composition for a color filter of the invention may be applied to the support by various coating methods such as slit coating, inkjet method, spin coating, cast coating, roll coating, and screen printing.

The thickness of the coating film of the curable composition is preferably from 0.1 to 3μ

The coating of the curable composition for a color filter on the support is generally dried under the conditions of 70 to 110° C. for 2 to 15 minutes to form a colored curable composition layer.

The exposure is preferably performed by irradiation with light using a (super) high-pressure mercury lamp or a laser.

The alkali developer is e.g ammonia water, organic alkaline compounds such as ethylamine, diethylamine, dimethyl-ethanolamine, triethanolamine, diethanolamine, monoethanolamine, morpholine, alkali metal hydroxides such as sodium hydroxide and potassium hydroxide, alkali metal carbonates such as sodium carbonate and potassium carbonate, alkali metal bicarbonates such as sodium bicarbonate and potassium bicarbonate, alkali metal silicates such as sodium silicate and potassium silicate, alkali metal metasilicates such as sodium metasilicate and potassium metasilicate, tetraalkylammonium hydroxides such as tetramethylammonium hydroxide, or trisodium phosphate. The concetration of the alkaline substance is 0.01 to 30 weight %, and pH is preferably 8 to 14.

The photosensitive or thermosetting composition of the present invention can also be used to form such overcoat layers, because a cured film of the composition is excellent in flatness, hardness, chemical and thermal resistance, transparency especially in a visible region, adhesion to a substrate, and suitability for forming a transparent conductive film, e.g., an ITO film, thereon. In the production of a protective layer, there has been a demand that unnecessary parts of the protective layer, for example on scribing lines for cutting the substrate and on bonding pads of solid image sensors should be removed from the substrate as described in JP57-42009-A, JP1-130103-A and JP1-134306-A. In this regard, it is difficult to selectively form a protective layer with good precision using the above-mentioned thermosetting resins. The photosensitive composition, however, allows to easily remove the unnecessary parts of the protective layer by photolithography.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. By using photolithographic process, columns of a resin can be formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the nonimaging area under black matrix of color filter elements. Therefore, the spacers formed using photosensitive compositions do not decrease brightness and optical aperture.

Photosensitive compositions for producing protective layer with spacers for color filters are disclosed in JP 2000-81701-A and dry film type photoresists for spacer materials are also disclosed in JP 11-174459-A and JP 11-174464-A. As described in the documents, the photosensitive compositions, liquid and dry film photoresists, are comprising at least an alkaline or acid soluble binder polymer, a radically polymerizable monomer, and a radical initiator. In some cases, thermally crosslinkable components such as epoxide and carboxylic acid may additionally be included.

The steps to form spacers using a photosensitive composition are as follows:
a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a postbaking is carried out to thermally cure the composition.

The photocurable compositions according to the invention are suitable for producing spacers for liquid crystal displays (as described above).

The compositions according to the invention are also suitable for manufacturing interlayer insulating layers or dielectric layers in a liquid crystal display, and more particularly in specific LCD structures such as color filter on array type and reflection type LCDs.

EXAMPLES

Preparation of NOR4: 9-Acetoxyoxymethyl-3-ethyl-8,8,10,10-tetramethyl-1,5-dioxa-9-azaspiro[5,5]undec-3-yl 4,7,10,13-tetraoxaheptadecanoate is prepared as described in the following scheme.

solution, and the reaction mixture is heated to reflux for 2 h (hours). After acidifying to pH 3 with diluted HCl aq. solution, EtOAc (ethyl acetate) is added to the mixture. The extract with EtOAc is concentrated, and the residue is applied to silica gel column with $CH_2Cl_2$-MeOH (methylene chloride-methanol) mixture as eluent. I1 is obtained as colorless oil, 5.34 g.

Preparation of I3

765 mg of oxalyl chloride is added to 838 mg of I1 in $CH_2Cl_2$ (7.5 mL), and the mixture is stirred at room temperature overnight. After concentration, the residue is dissolved in 3 mL of toluene and added to I2 (for method of preparation, see JP1979020977B) in toluene (10 mL). The reaction mixture is heated at 50° C. for 4.5 h, and then treated with $K_2CO_3$ aq. solution. The organic layer is separated and then purified by silica gel column with $CH_2Cl_2$-MeOH mixture as eluent. 860 mg of a colorless oil are obtained.

Preparation of NOR4

602 mg of I3 are dissolved in 4.5 mL of toluene, and 2.095 g of $NaHCO_3$ and 4.5 mL of $H_2O$ are added. To this mixture are added 1.57 g of 9% peracetic acid solution in acetic acid over 10 min. at room temperature. After stirring for 4 h, 112 mg of $Na_2SO_3$ are added. The resulting I4 is extracted with ethyl acetate (EtOAc). After concentration, the residue is dissolved in 1.5 mL of toluene, and 0.1 mL of 50% hydroxylamine aq. solution are added. The mixture is heated at 80° C. for 1 h. The reaction mixture is cooled down, and 1 mL of toluene and 1 mL of $H_2O$ are added. The toluene layer is separated, and 170 mg of acetic anhydride in 0.5 mL of toluene are added. The reaction mixture is stirred at room temperature for 2 hours (2 h) and treated with aqueous potas-

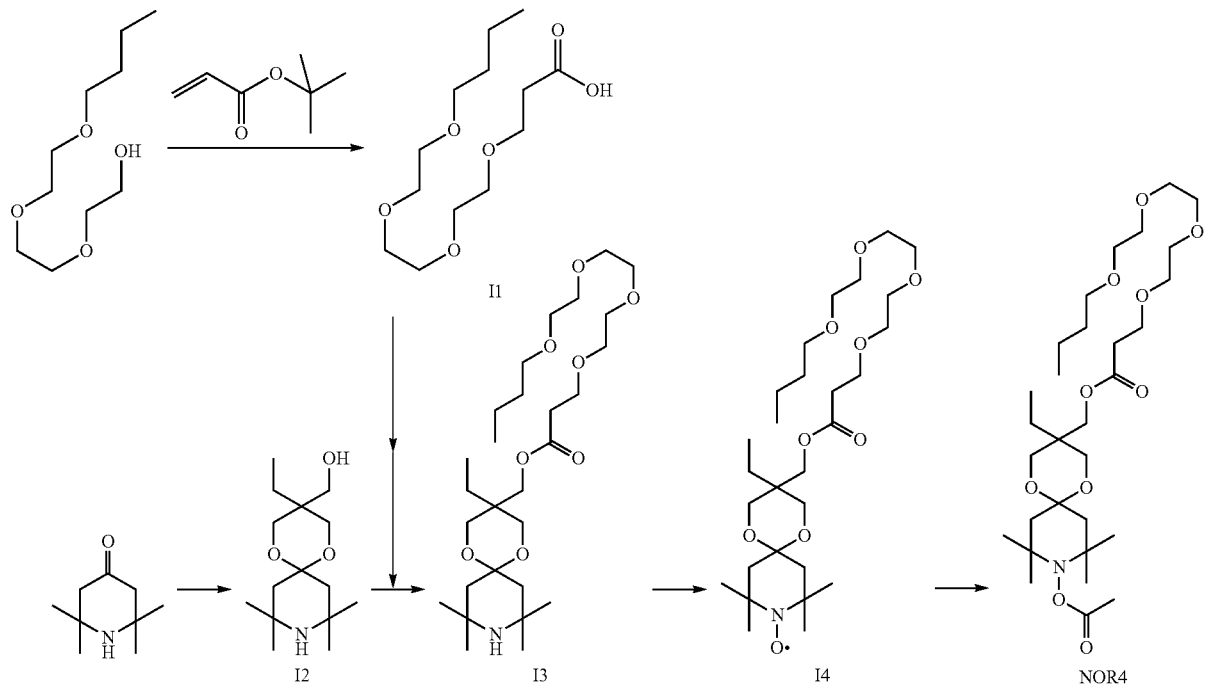

Preparation of 4,7,10,13-tetraoxaheptadecanoic acid (I1)

To 4.13 g of triethylene glycol mono-n-butyl ether in toluene (150 mL) are added 264 mg of t-BuOK (potassium tert-butanolate) in portions and then 5.81 g of t-butyl acrylate in toluene (20 mL) at room temperature. The mixture is stirred at room temperature overnight, and toluene is removed in vacuo. To this residue are added 40 mL of 0.5 N KOH ethanol sium carbonate ($K_2CO_3$ aq.) solution and then aqueous $Na_2S_2O_4$ solution. The organic layer is separated and then purified by silica gel column with $CH_2Cl_2$-methanol mixture as eluent. 514 mg of NOR4 are obtained as colorless oil: $^1$H-NMR (CDCl$_3$/TMS, δ ppm), 0.82 (t, 3H), 0.91 (t, 3H), 1.04-1.64 (m, 18H), 2.10 (s, 3H), 1.64-2.50 (m, 4H), 2.62 (t, 2H).

Example 2

Preparation of NOR

Analogously as described in Example 1 NOR2, NOR3, NOR5 (colorless oil), NOR6, NOR9, and NOR13-26 are prepared. The $^1$H-NMR (CDCl$_3$/TMS, δ ppm) data are described below.

NOR2: 0.79-2.86 (m, 60H), 3.52-4.39 (m, 5H), NOR3: 0.79-2.32 (m, 60H), 3.70-4.35 (m, 5H), NOR5: 0.75-2.2 (m, 37H), 2.4-2.9 (m, 2H), 3.46 (t, 2H), 3.5-4.5 (m, 20H), NOR6: 0.79-2.85 (m, 53H), 3.52-4.39 (m, 6H), NOR9: 0.80-2.92 (m, 71H), 3.54-4.42 (m, 6H), NOR13: 0.82-2.44 (m, 59H), 3.59-4.19 (m, 6H), NOR14: 0.79-2.85 (m, 65H), 3.48-4.40 (m, 6H), NOR15: 0.72-2.85 (m, 97H), 3.48-4.39 (m, 6H), NOR16: 0.82-2.45 (m, 59H), 3.60-3.67 (m, 4H), 4.20 (q, 2H), NOR17: 0.80-2.86 (m, 65H), 3.50-4.39 (m, 6H), NOR18: 0.82 (t, 3H), 1.09 (d, 6H), 1.27 (s, 6H), 1.27-2.10 (s, 12H), 3.59-3.67 (m, 4H), 4.21 (q, 2H), NOR19: 0.82-2.44 (m, 65H), 3.59-3.68 (m, 4H), 4.19 (q, 2H), NOR20: 0.88-2.87 (m, 27H), 2.05 (s, 3H), 3.57-4.68 (m, 6H), NOR21: 0.87-2.88 (m, 27H), 2.06 (s, 3H), 3.65-4.64 (m, 6H), 3.91 (s, 9H), 7.28 (s, 1H), 7.30 (s, 1H), NOR22: 1.15 (s, 6H), 1.27-1.28 (m, 9H), 1.41 (d, 6H), 2.13 (s, 3H), 2.17-2.23 (m, 4H), 6.64-6.69 (m, 1H), 6.79 (dd, 1H), 6.83-6.84 (m, 1H), NOR23: 0.87-2.81 (m, 30H), 3.45-4.54 (m, 9H), 6.94-6.97 (m, 2H), 7.98-8.02 (m, 2H), NOR24: 0.86-2.7 (m, 27H), 3.7-4.65 (m, 24H), 7.28-7.32 (m, 4H), NOR25: 0.79-2.61 (m, 27H), 2.04 (s, 3H), 3.53-4.44 (m, 6H), 5.16 (d, 2H), 7.32-7.41 (m, 5H), NOR26: 0.8-2.88 (m, 30H), 2.04 (s, 3H), 2.63-2.66 (m, 4H), 3.45-4.44 (m, 8H).

NOR7, 8, 10-12 and NOR27 are known compounds described in the previous Ciba patent application WO0190113A1 (cf. also U.S. Pat. No. 4,105,626A).

Application Examples

Thermal Radical Initiators Tested

| Thermal radical initiator (TRI) | Structure |
|---|---|
| NOR1 | 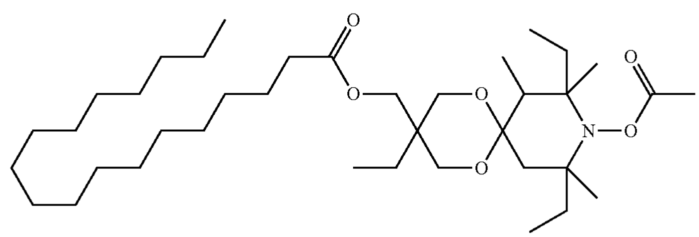 [SMILES: CCCCCCCCCCCCCCCCCC(=O)OCC1(CC)COC2(CC(C)(CC)N(OC(C)=O)C(C)(CC)C2C)OC1] |
| NOR2 | 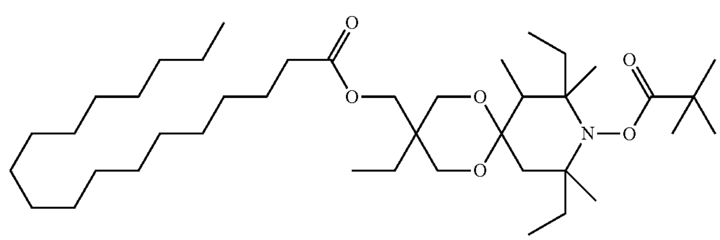 [SMILES: CCCCCCCCCCCCCCCCCC(=O)OCC1(CC)COC2(CC(C)(CC)N(OC(=O)C(C)(C)C)C(C)(CC)C2C)OC1] |
| NOR3 | 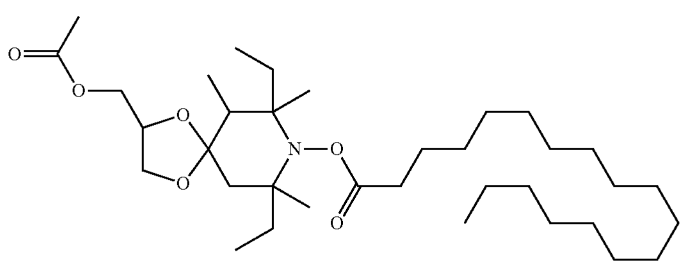 [SMILES: CCCCCCCCCCCCCCCCCC(=O)ON1C(C)(CC)CC2(OCC(COC(C)=O)O2)C(C)C1(C)CC] |
| NOR5 | 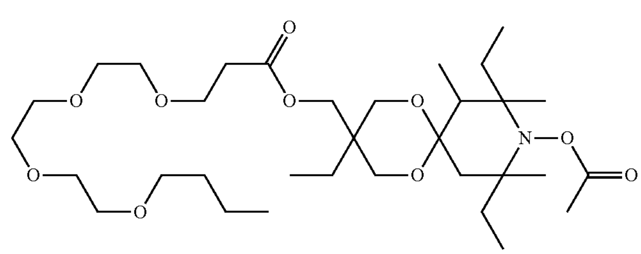 [SMILES: CCCCOCCOCCOCCOCCC(=O)OCC1(CC)COC2(CC(C)(CC)N(OC(C)=O)C(C)(CC)C2C)OC1] |

-continued
| Thermal radical initiator (TRI) | Structure |
|---|---|
| NOR6 | 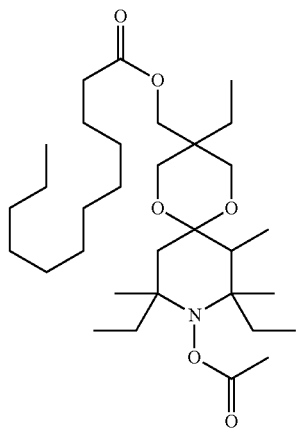 [SMILES: CCCCCCCCCCCC(=O)OCC1(CC)COC2(CC(C)(CC)N(OC(C)=O)C(C)(CC)C2C)OC1] |
| NOR7 | 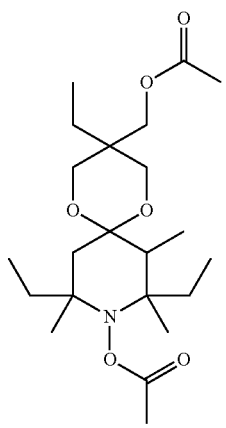 [SMILES: CCC1(COC(C)=O)COC2(CC(C)(CC)N(OC(C)=O)C(C)(CC)C2C)OC1] |
| NOR8 | 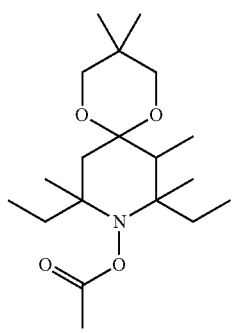 [SMILES: CCC1(C)CC2(OCC(C)(C)CO2)C(C)C(C)(CC)N1OC(C)=O] |
| NOR9 | 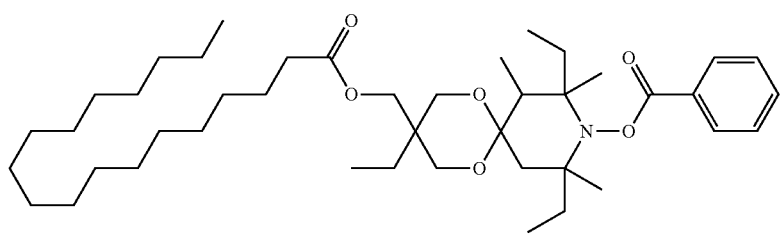 [SMILES: CCCCCCCCCCCCCCCCCC(=O)OCC1(CC)COC2(CC(C)(CC)N(OC(=O)c3ccccc3)C(C)(CC)C2C)OC1] |

-continued
| Thermal radical initiator (TRI) | Structure |
|---|---|
| NOR10 | 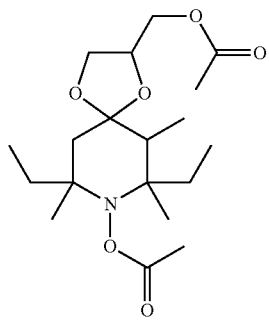 [SMILES: CCC1(C)CC2(OCC(COC(C)=O)O2)C(C)C(C)(CC)N1OC(C)=O] |
| NOR11 | 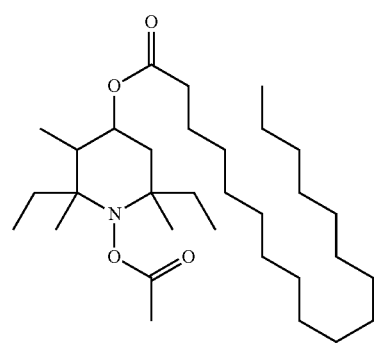 [SMILES: CCCCCCCCCCCCCCCCCC(=O)OC1CC(C)(CC)N(OC(C)=O)C(C)(CC)C1C] |
| NOR12 | 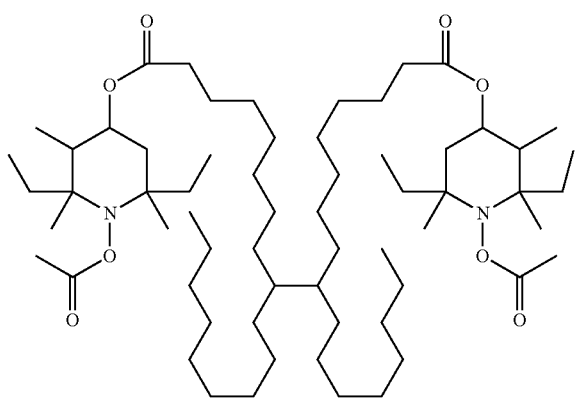 [SMILES: CCCCCCCCCC(CCCCCCCC(=O)OC1CC(C)(CC)N(OC(C)=O)C(C)(CC)C1C)C(CCCCCCCC)CCCCCCCC(=O)OC1CC(C)(CC)N(OC(C)=O)C(C)(CC)C1C] |
| NOR13 | 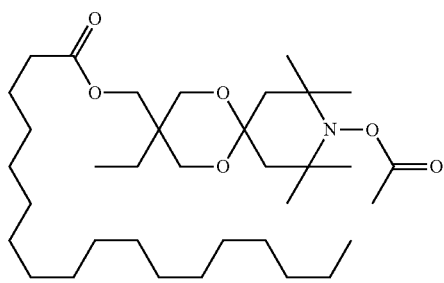 [SMILES: CCCCCCCCCCCCCCCCCC(=O)OCC1(CC)COC2(CC(C)(C)N(OC(C)=O)C(C)(C)C2)OC1] |
| NOR14 | 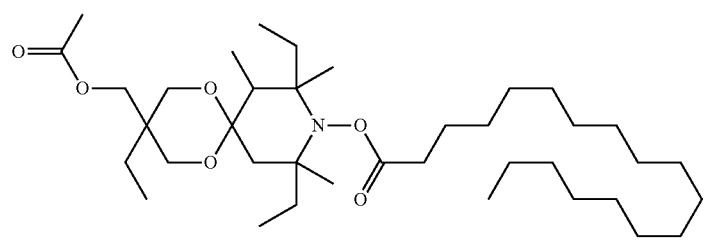 [SMILES: CCCCCCCCCCCCCCCCCC(=O)ON1C(C)(CC)CC2(OCC(CC)(COC(C)=O)CO2)C(C)C1(C)CC] |

-continued
| Thermal radical initiator (TRI) | Structure |
|---|---|
| NOR15 | 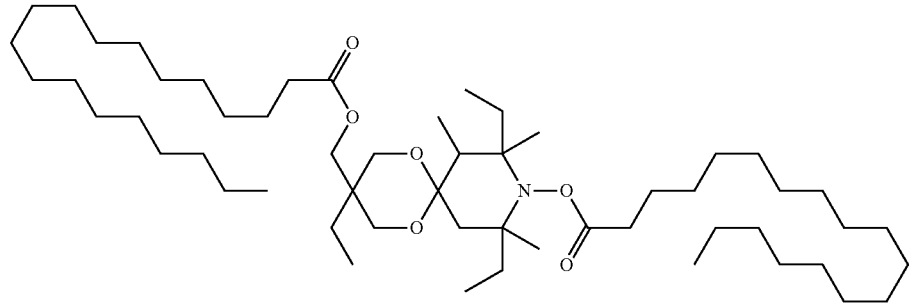 [SMILES: CCCCCCCCCCCCCCCCCCC(=O)OCC1(CC)COC2(CC(C)(CC)N(OC(=O)CCCCCCCCCCCCCCCCC)C(C)(CC)C2C)OC1] |
| NOR16 | 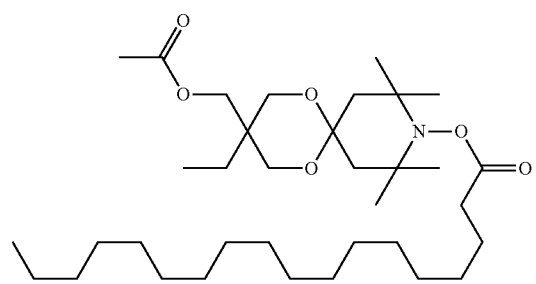 [SMILES: CCCCCCCCCCCCCCCCCC(=O)ON1C(C)(C)CC2(CC1(C)C)OCC(CC)(COC(C)=O)CO2] |
| NOR17 | 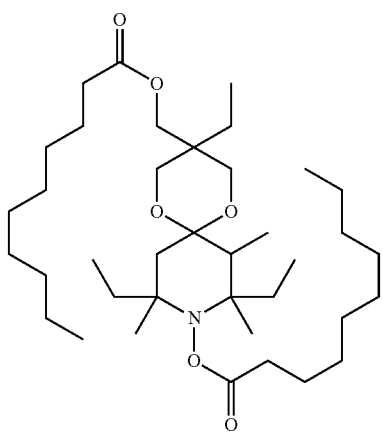 [SMILES: CCCCCCCCCC(=O)OCC1(CC)COC2(CC(C)(CC)N(OC(=O)CCCCCCCCC)C(C)(CC)C2C)OC1] |
| NOR18 | 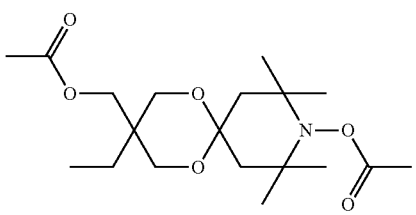 [SMILES: CCC1(COC(C)=O)COC2(CC(C)(C)N(OC(C)=O)C(C)(C)C2)OC1] |
| NOR19 | 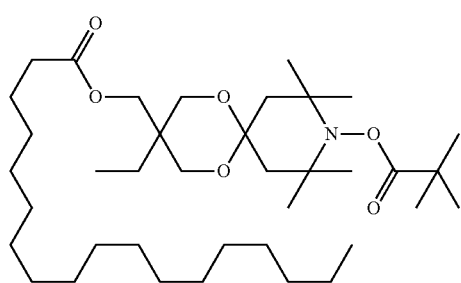 [SMILES: CCCCCCCCCCCCCCCCCC(=O)OCC1(CC)COC2(CC(C)(C)N(OC(=O)C(C)(C)C)C(C)(C)C2)OC1] |

| Thermal radical initiator (TRI) | Structure |
|---|---|
| NOR20 | 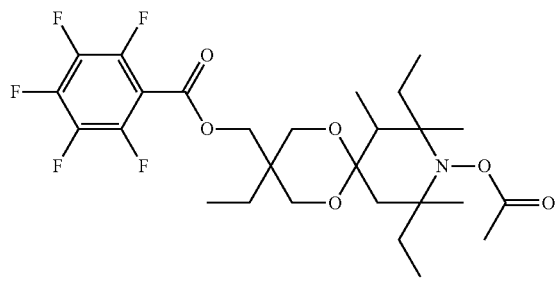 [SMILES: CCC1(COC(=O)c2c(F)c(F)c(F)c(F)c2F)COC2(CC(C)(CC)N(OC(C)=O)C(C)(CC)C2C)OC1] |
| NOR21 | 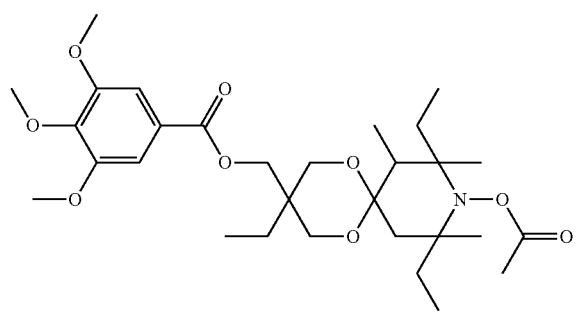 [SMILES: CCC1(COC(=O)c2cc(OC)c(OC)c(OC)c2)COC2(CC(C)(CC)N(OC(C)=O)C(C)(CC)C2C)OC1] |
| NOR22 | 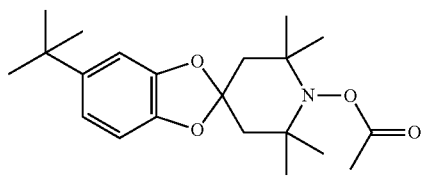 [SMILES: CC(=O)ON1C(C)(C)CC2(CC1(C)C)Oc1ccc(C(C)(C)C)cc1O2] |
| NOR23 | 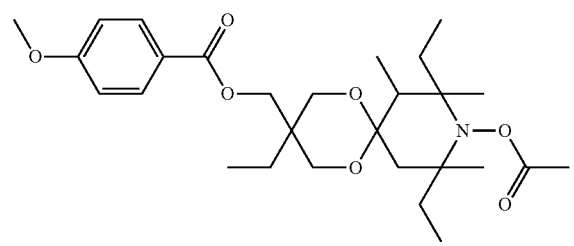 [SMILES: CCC1(COC(=O)c2ccc(OC)cc2)COC2(CC(C)(CC)N(OC(C)=O)C(C)(CC)C2C)OC1] |
| NOR24 | 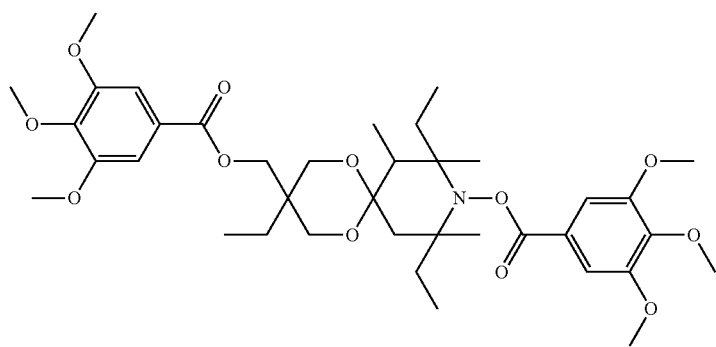 |

| Thermal radical initiator (TRI) | Structure |
|---|---|
| NOR25 | 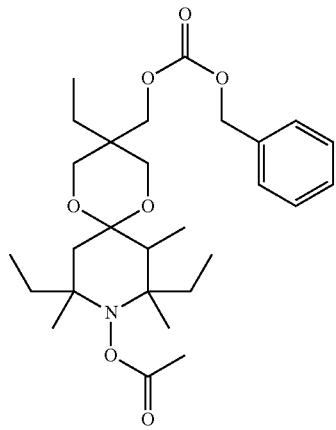 [SMILES: CCC1(COC(=O)OCc2ccccc2)COC2(CC(C)(CC)N(OC(C)=O)C(C)(CC)C2C)OC1] |
| NOR26 | 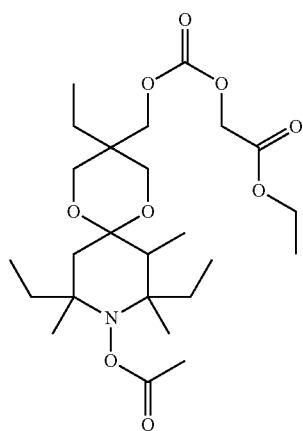 [SMILES: CCOC(=O)COC(=O)OCC1(CC)COC2(CC(C)(CC)N(OC(C)=O)C(C)(CC)C2C)OC1] |
| NOR27 | 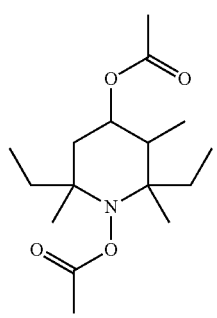 [SMILES: CCC1(C)CC(OC(C)=O)C(C)C(C)(CC)N1OC(C)=O] |
| Peroxide1 | 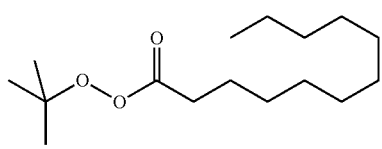 [SMILES: CCCCCCCCCCCC(=O)OOC(C)(C)C] |
| Peroxide2 | 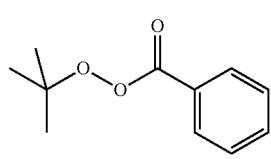 |

| Thermal radical initiator (TRI) | Structure |
|---|---|
| Peroxide3 | 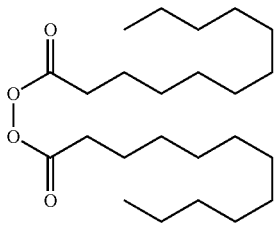 [SMILES: CCCCCCCCCCCC(=O)OOC(=O)CCCCCCCCCCC] |

Preparation of Color Filter Resist (Blue)

Blue pigment dispersion is prepared by mixing the following components and dispersing them by using a Paint conditioner (SKANDEX).

Blue Dispersion

- 6.1 parts by weight blue pigment (PB15:6, Blue E provided by Toyo Ink)
- 2.2 parts by weight dispersant (Ajisper PB821 provided by Ajinomoto Fine Techno)
- 0.2 parts by weight synergist (Solsperse S5000 provided by Lubrizol)
- 71.0 parts by weight solvent (PGMEA)

Radically polymerizable color filter resist (blue) are prepared by further adding the following components to the above dispersion prepared.

- 14.4 parts by weight alkaline developable binder (alkaline developable resin), 37.8% solution (Ripoxy SPC-2000, provided by Showa Highpolymer)
- 6.1 parts by weight multifunctional acrylate (DPHA, provided by UCB Chemicals)

Thermal Curing Tests of Blue Color Filter Resist after Photocuring

The hydroxylamine ester to be tested and additionally Ciba® IRGACURE® 369 (4.8 wt % in solid) as photoinitiator are added to the above color filter resist composition and mixed. The composition is applied to a silicon wafer using a spin coater (1H-DX2, MIKASA). The solvent is removed by heating at 90° C. for 2.5 min in a convection oven. The thickness of the dry film is approximately 1.2 μm. Exposure is then carried out using a 250 W super high pressure mercury lamp (USHIO, USH-250BY) at a distance of 15 cm. The total exposure dose determined by measuring light intensity with an optical power meter (ORC UV Light Measure Model UV-M02 with UV-35 detector) is 150 mJ/cm². The coating is further baked at 180° C. for 30 min (minutes), at 230° C. for 4 min, or at 230° C. for 30 min. The conversion of acrylic double bond is determined by measuring IR absorption at 810 cm⁻¹ with a FT-IR spectrometer (FT-720, HORIBA) before exposure and after baking. The higher the conversion, the more active is the tested hydroxylamine ester. The results of the tests are given in the following table.

| Thermal radical initiator (TRI) | Concentration of TRI (mol/kg in composition) | Baking conditions | C = C conversion (%) |
|---|---|---|---|
| NOR1 | 0.02 | 180° C. for 30 min | 78.8 |
| NOR2 | 0.02 | 180° C. for 30 min | 81.3 |
| NOR3 | 0.02 | 180° C. for 30 min | 88.1 |
| NOR4 | 0.02 | 180° C. for 30 min | 69.9 |
| NOR5 | 0.02 | 180° C. for 30 min | 88.3 |
| NOR6 | 0.02 | 180° C. for 30 min | 72.3 |
| NOR9 | 0.02 | 180° C. for 30 min | 84.5 |
| NOR10 | 0.02 | 180° C. for 30 min | 65.0 |
| NOR11 | 0.02 | 180° C. for 30 min | 68.9 |
| NOR12 | 0.02 | 180° C. for 30 min | 64.2 |
| NOR13 | 0.02 | 180° C. for 30 min | 66.4 |
| NOR14 | 0.02 | 180° C. for 30 min | 81.5 |
| NOR15 | 0.02 | 180° C. for 30 min | 80.6 |
| NOR17 | 0.02 | 180° C. for 30 min | 68.6 |
| NOR19 | 0.02 | 180° C. for 30 min | 71.2 |
| NOR20 | 0.02 | 180° C. for 30 min | 67.6 |
| NOR21 | 0.02 | 180° C. for 30 min | 73.6 |
| NOR23 | 0.02 | 180° C. for 30 min | 64.0 |
| NOR24 | 0.02 | 180° C. for 30 min | 74.6 |
| NOR25 | 0.02 | 180° C. for 30 min | 69.9 |
| NOR26 | 0.02 | 180° C. for 30 min | 75.2 |
| NOR27 | 0.02 | 180° C. for 30 min | 68.1 |
| NOR1 | 0.02 | 230° C. for 4 min | 82.1 |
| NOR2 | 0.02 | 230° C. for 4 min | 83.2 |
| NOR3 | 0.02 | 230° C. for 4 min | 79.7 |
| NOR5 | 0.02 | 230° C. for 4 min | 83.6 |
| NOR7 | 0.02 | 230° C. for 30 min | 80.8 |
| NOR8 | 0.02 | 230° C. for 30 min | 81.4 |
| NOR16 | 0.02 | 230° C. for 30 min | 86.0 |
| NOR18 | 0.02 | 230° C. for 30 min | 81.4 |
| NOR22 | 0.02 | 230° C. for 30 min | 81.5 |

Comparison:

| Thermal radical initiator (TRI) | Concentration of TRI (mol/kg in composition) | Baking conditions | C = C conversion (%) |
|---|---|---|---|
| No TRI | 0 | 180° C. for 30 min | 60.6 |
| No TRI | 0 | 230° C. for 30 min | 79.7 |
| Peroxide1 | 0.07 | 180° C. for 30 min | 57.0 |
| Peroxide2 | 0.1 | 180° C. for 30 min | 56.4 |
| Peroxide3 | 0.03 | 180° C. for 30 min | 49.0 |

The invention claimed is:

1. A method for producing a color filter comprising:
   I) applying a radically polymerizable composition on a support,
   wherein the radically polymerizable composition comprises:
   (a) at least one alkaline developable resin;
   (b) at least one acrylate monomer;
   (c) at least one photoinitiator; and
   (d) at least one hydroxylamine ester compound of formula I

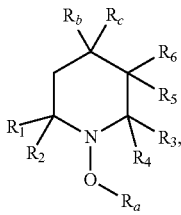

(I)

wherein
- $R_a$ represents an acyl radical;
- one of $R_b$ and $R_c$ represents hydrogen and the other one represents a substituent; or
- $R_b$ and $R_c$ both represent hydrogen or identical or different substituents; or
- $R_b$ and $R_c$ together represent oxygen; or
- $R_b$ and $R_c$ together form a ring;
- $R_1$-$R_4$ each represent $C_1$-$C_6$alkyl; and
- $R_5$ and $R_6$ each represent independently of one another hydrogen, $C_1$-$C_6$alkyl or $C_6$-$C_{10}$aryl; or $R_5$ and $R_6$ together represent oxygen;

II) drying the photopolymerizable composition;
III) exposing the photopolymerizable composition to UV light through a mask;
IV) developing the exposed composition layer with an alkali developer to form a colored pattern; and
V) post baking the exposed photoresist at 180 to 230° C.

2. A method for producing a color filter comprising:
I) applying a radically polymerizable composition to a support,
wherein the radically polymerizable composition comprises:
(a) at least one alkaline developable resin;
(b) at least one acrylate monomer;
(c) at least a photoinitiator;
(d) at least one hydroxylamine ester compound of formula IA'

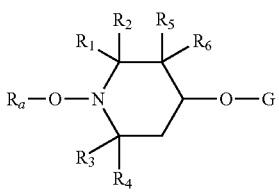

(IA')

or a hydroxylamine-ester of the formula IC'

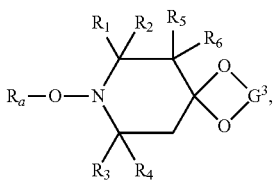

(IC')

wherein
in formula (IA')
$R_1$-$R_4$ each represent $C_1$-$C_6$alkyl; and
$R_5$ and $R_6$ each represent independently of one another hydrogen, $C_1$-$C_6$alkyl or $C_6$-$C_{10}$aryl; or $R_5$ and $R_6$ together represent oxygen,
Ra is an acyl radical selected from —C(=O)—H, —C(=O)—$C_1$-$C_{32}$alkyl, —C(=O)—$C_2$-$C_{32}$alkenyl, —C(=O)—$C_2$-$C_4$alkylene-$C_6$-$C_{10}$aryl, C(=O)—$C_2$-$C_4$alkylene-C(=O)—$C_1$-$C_{32}$alkyl, —C(=O)—$C_6$-$C_{10}$aryl, —C(=O)—O—$C_1$-$C_{32}$alkyl, —C(=O)—O—benzyl, —C(=O)—O—$C_6$-$C_{10}$aryl, —C(=O)—NH—$C_1$-$C_{32}$alkyl, —C(=O)—NH—$C_6$-$C_{10}$aryl and —C(=O)—N($C_1$-$C_{32}$alkyl)$_2$, wherein $C_1$-$C_{32}$alkyl and $C_6$-$C_{10}$aryl may be optionally interrupted by one or more O or C=O and/or substituted by one or more halogen, $OR_9$, $COOR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$; wherein $R_9$ and $R_{10}$ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O;
G is $C_1$-$C_{32}$alkyl or —C(=O)—$C_1$-$C_{32}$alkyl, wherein $C_1$-$C_{32}$alkyl is interrupted by one or more C=O and/or substituted by one or more halogen, $OR_9$, $COOR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$; or
G is —C(=O)—$C_4$-$C_{20}$cycloalkyl, —C(=O)—$C_2$-$C_{32}$alkenyl, —C(=O)—$C_2$-$C_4$alkylene-$C_6$-$C_{10}$aryl, —C(=O)—$C_2$-$C_4$alkylene-C(=O)$C_1$-$C_{32}$alkyl, or —C(=O)—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, $OR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$ and/or $C_1$-$C_{32}$alkyl and $C_4$-$C_{20}$cycloalkyl may be interrupted by one or more O or C=O; or $C_4$-$C_{20}$cycloalkyl, —C(=O)—O—$C_1$-$C_{32}$alkyl, —C(=O)—O—$C_6$-$C_{10}$aryl, —C(=O)—NH—$C_1$-$C_{32}$alkyl, —C(=O)—NH—$C_6$-$C_{10}$aryl, —C(=O)—N($C_1$-$C_{32}$alkyl)$_2$ or —C(=S)—NH—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, $OR_9$, $COOR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$ and/or $C_1$-$C_{32}$alkyl and $C_4$-$C_{20}$cycloalkyl may be interrupted by one or more O or C=O;
$R_9$ and $R_{10}$ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O,
in formula (IC')
$R_1$-$R_4$ each represent $C_1$-$C_6$alkyl; and
$R_5$ and $R_6$ each represent independently of one another hydrogen, $C_1$-$C_6$alkyl or $C_6$-$C_{10}$aryl; or $R_5$ and $R_6$ together represent oxygen,
Ra is an acyl radical selected from —C(=O)—H, —C(=O)—$C_1$-$C_{32}$alkyl, —C(=O)—$C_2$-$C_{32}$alkenyl, —C(=O)—$C_2$-$C_4$alkylene-$C_6$-$C_{10}$aryl, C(=O)—$C_2$-$C_4$alkylene-C(=O)—$C_1$-$C_{32}$alkyl, —C(=O)—$C_6$-$C_{10}$aryl, —C(=O)—O—$C_1$-$C_{32}$alkyl, —C(=O)—O—benzyl, —C(=O)—O—$C_6$-$C_{10}$aryl, —C(=O)—NH—$C_1$-$C_{32}$alkyl, —C(=O)—NH—$C_6$-$C_{10}$aryl and —C(=O)—N($C_1$-$C_{32}$alkyl)$_2$, wherein $C_1$-$C_{32}$alkyl and $C_6$-$C_{10}$aryl may be optionally interrupted by one or more O or C=O and/or substituted by one or more halogen, $OR_9$, $COOR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$; wherein $R_9$ and $R_{10}$ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O;

$G^3$ is $C_2$-$C_8$alkylene substituted by one or more $OR_7$, $C_2$-$C_8$hydroxyalkylene substituted by one or more $OR_8$; 1,2-phenylene or 1-methylene-2-phenyl, each of which optionally is substituted by one or more $C_1$-$C_{20}$alkyl, halogen, phenyl, $OR_8$, $COOR_9$, $CONR_9R_{10}$ or $C_1$-$C_{20}$alkyl interrupted by one or more O and/or substituted by halogen or $OR_8$; with $R_7$ is $C_1$-$C_{32}$alkyl, $C_4$-$C_{20}$cycloalkyl, —C(=O)—$C_4$-$C_{20}$cycloalkyl, —C(=O)—$C_2$-$C_{32}$alkenyl, —C(=O)—$C_2$-$C_4$alkenyl-$C_6$-$C_{10}$aryl, —C(=O)—$(CH_2)_{1-4}$—C(=O)—$C_1$-$C_{32}$alkyl, —C(=O)—$C_6$-$C_{10}$aryl, —C(=O)-benzyl, —C(=O)—O—$C_1$-$C_{32}$alkyl, —C(=O)—O—$C_6$-$C_{10}$aryl, —C(=O)—NH—$C_1$-$C_{32}$alkyl, —C(=O)—NH—$C_6$-$C_{10}$aryl, —C(=O)—N($C_1$-$C_{32}$alkyl)$_2$ or —C(=S)—NH—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, $OR_8$, $COOR_8$, $CONR_8R_9$, phenyl or phenyl substituted by halogen, $C_1$-$C_{32}$alkyl, $C_1$-$C_4$haloalkyl, $SR_8$, $OR_8$, or $NR_8R_9$ and/or $C_1$-$C_{32}$alkyl and $C_4$-$C_{20}$cycloalkyl may be interrupted by one or more O or C=O; or —C(=O)—$C_1$-$C_{32}$alkyl, which is interrupted by one or more O or C=O and/or substituted by one or more halogen, $OR_8$, $COOR_8$, $CONR_8R_9$, phenyl or phenyl substituted by halogen, $C_1$-$C_{32}$alkyl, $C_1$-$C_4$haloalkyl, S $R_8$, $OR_8$, or $NR_8R_9$;

$R_8$ is hydrogen, $C_1$-$C_{32}$alkyl, $C_4$-$C_{20}$cycloalkyl, —C(=O)—$C_1$-$C_{32}$alkyl, —C(=O)—$C_4$-$C_{20}$cycloalkyl, —C(=O)—$C_2$-$C_{32}$alkenyl, —C(=O)—$C_2$-$C_4$alkenyl-$C_6$-$C_{10}$aryl, —C(=O)—$C_6$-$C_{10}$aryl, —C(=O)—O—$C_1$-$C_{32}$alkyl, —C(=O)—O—$C_6$-$C_{10}$aryl, —C(=O)—NH—$C_1$-$C_{32}$alkyl, —C(=O)—NH—$C_6$-$C_{10}$aryl, —C(=O)—N($C_1$-$C_{32}$alkyl)$_2$ or —C(=S)—NH—$C_6$-$C_{10}$aryl, wherein $C_1$-$C_{32}$alkyl, $C_4$-$C_{20}$cycloalkyl and $C_6$-$C_{10}$aryl may be optionally substituted by one or more halogen, $OR_9$, $COOR_9$, $CONR_9R_{10}$, phenyl or phenyl substituted by halogen, $C_1$-$C_{32}$alkyl, $C_1$-$C_4$haloalkyl, $SR_9$, $OR_9$, or $NR_9R_{10}$ and/or $C_1$-$C_{32}$alkyl and $C_4$-$C_{20}$cycloalkyl may be interrupted by one or more O or C=O;

$R_9$ and $R_{10}$ independently of one another are hydrogen or unsubstituted or substituted $C_1$-$C_{32}$alkyl, $C_6$-$C_{10}$aryl, $C_4$-$C_{10}$heteroaryl, $C_7$-$C_{20}$aralkyl or $C_4$-$C_{20}$cycloalkyl, whereby the alkyl and cycloalkyl are uninterrupted or interrupted by O;

II) drying the photopolymerizable composition;

III) exposing the photopolymerizable composition to UV light through a mask;

IV) developing the exposed composition layer with an alkali developer to form a colored pattern; and V) post baking the exposed photoresist at 180 to 230° C.

* * * * *